United States Patent
Frisch et al.

(10) Patent No.: US 12,360,263 B2
(45) Date of Patent: Jul. 15, 2025

(54) POSITRON EMISSION TOMOGRAPHY SYSTEMS BASED ON IONIZATION-ACTIVATED ORGANIC FLUOR MOLECULES, PLANAR PIXELATED PHOTODETECTORS, OR BOTH

(71) Applicant: The University of Chicago, Chicago, IL (US)

(72) Inventors: Henry J. Frisch, Chicago, IL (US); Evan Angelico, San Marcos, CA (US); Patrick J. La Riviere, Chicago, IL (US); Bernhard W. Adams, Naperville, IL (US); Eric Spieglan, Lisle, IL (US); Joao F. Shida, Sao Paulo (BR); Andrey Elagin, Bolingbrook, IL (US); Kepler Domurat-Sousa, East Lansing, MI (US); Allison H. Squires, Chicago, IL (US)

(73) Assignee: THE UNIVERSITY OF CHICAGO, Chicago, IL (US)

( * ) Notice: Subject to any disclaimer, the term of this patent is extended or adjusted under 35 U.S.C. 154(b) by 291 days.

(21) Appl. No.: 18/033,709

(22) PCT Filed: Oct. 26, 2021

(86) PCT No.: PCT/US2021/056535
§ 371 (c)(1),
(2) Date: Apr. 25, 2023

(87) PCT Pub. No.: WO2022/093732
PCT Pub. Date: May 5, 2022

(65) Prior Publication Data
US 2023/0400595 A1    Dec. 14, 2023

Related U.S. Application Data

(60) Provisional application No. 63/106,665, filed on Oct. 28, 2020.

(51) Int. Cl.
*G01T 1/29* (2006.01)
*A61B 6/00* (2024.01)
(Continued)

(52) U.S. Cl.
CPC ............ *G01T 1/2985* (2013.01); *A61B 6/037* (2013.01); *A61B 6/4241* (2013.01);
(Continued)

(58) Field of Classification Search
CPC ...... G01T 1/2985; G01T 1/1647; A61B 6/037; A61B 6/4241; A61B 6/4258; A61B 6/5247; A61B 6/4266
See application file for complete search history.

(56) References Cited

U.S. PATENT DOCUMENTS

| | | | |
|---|---|---|---|
| 5,512,753 A | 4/1996 | Thomson et al. | |
| 6,087,656 A * | 7/2000 | Kimmich | G01T 1/40 250/363.01 |

(Continued)

OTHER PUBLICATIONS

Uno, Kakishi, et al. "In situ preparation of highly fluorescent dyes upon photoirradiation." *Journal of the American Chemical Society* 133.34 (2011): 13558-13564.
(Continued)

*Primary Examiner* — David P Porta
*Assistant Examiner* — Casey Bryant
(74) *Attorney, Agent, or Firm* — Bell & Manning, LLC

(57) ABSTRACT

Gamma-ray detectors for the detection of one or more gamma-rays are provided. Also provided are methods of using the detectors for the detection of one or more gamma-rays. The detectors can be used in high-spatial resolution PET systems, including time-of-flight (TOF)-PET systems. Some of the gamma-ray detectors utilize fluors and an optical imaging system to determine the time and location of a first scattering event of a gamma-ray in a low atomic
(Continued)

number scintillating medium. Some of the gamma-ray detectors determine the time and location of a first scattering event of a gamma-ray in a low-density scintillating medium by imaging scintillation photons from the scattering event as a time-series of photon "rings" using a planar pixelated photodetector as a scintillation photon counter.

21 Claims, 20 Drawing Sheets

(51) Int. Cl.
    A61B 6/03        (2006.01)
    A61B 6/42        (2024.01)
    G01T 1/164      (2006.01)
(52) U.S. Cl.
    CPC .......... *A61B 6/4258* (2013.01); *A61B 6/5247* (2013.01); *G01T 1/1647* (2013.01)

(56) References Cited

U.S. PATENT DOCUMENTS

| | | | |
|---|---|---|---|
| 8,115,176 | B2 * | 2/2012 | Stein .................... G01T 1/40 250/370.11 |
| 8,604,440 | B2 | 12/2013 | Frisch et al. |
| 10,132,942 | B2 | 11/2018 | Frisch et al. |
| 2008/0283725 | A1 | 11/2008 | Hahn et al. |
| 2011/0012021 | A1 | 1/2011 | Inbar |
| 2015/0331118 | A1 | 11/2015 | Iltis |
| 2016/0274237 | A1 | 9/2016 | Stutz |
| 2019/0000403 | A1 | 1/2019 | Chen |

OTHER PUBLICATIONS

Kim, Dojin, Ji Eon Kwon, and Soo Young Park. "Fully reversible multistate fluorescence switching: organogel system consisting of luminescent cyanostilbene and turn-on diarylethene." *Advanced Functional Materials* 28.7 (2018): 1706213.

Kashihara, Ryota, et al. "Fluorescence photoswitching of a diarylethene by irradiation with single-wavelength visible light." *Journal of the American Chemical Society* 139.46 (2017): 16498-16501.

Abe, F., et al. "The CDF detector: an overview." *Nuclear Instruments and Methods in Physics Research* Section A: Accelerators, Spectrometers, Detectors and Associated Equipment 271.3 (1988): 387-403.

Onken, Drew R., et al. "Time response of water-based liquid scintillator from X-ray excitation." *Materials Advances* 1.1 (2020): 71-76.

Jinseo Park, Fangjian Wu, Evan Angelico, Henry J. Frisch, Eric Spieglan, "Patterned anodes with sub-millimeter spatial resolution for large-area MCP-based photodetector systems," *Nuclear Inst. and Methods in Physics Research, A* 985 (2021) 164702; Sep. 22, 2020.

E. Oberla, "PSEC4 waveform sampler & Large-Area Picosecond Photo-Detectors readout electronics,": in proceedings of the Workshop on Picosecond Photon Sensors, Clermont-Ferrand, Mar. 12, 2014; pp. 1-34.

E. Oberla, J. Porter, and J. Stanoviak; "PSEC4A: A 10 GSa/s Waveform Sampling ASIC with Multi-Event Buffering Capability," Proceedings of TWEPP 2018; Antwerp, Belgium (Sep. 2018).

Simon R. Cherry et al., "PET: Physics, Instrumentation, and Scanners," (2006), pp. 1-117. 10.1007/0-387-34946-4_1.

K. Kleinknecht, "Particle Detectors," *Physics Reports (Review Section of Physics Letters* 84, No. 2 (1982); pp. 85-161. North-Holland Publishing Company.

A. Gando et al., "Search for Majorana Neutrinos Near the Inverted Mass Hierarchy Region with KamLAND-Zen," *Phys. Rev. Lett.* 117, 082503—Published Aug. 16, 2016. DOI: 10.1103/PhysRevLett. 117.082503.

Masahiro Irie et al., "Photoswitchable Turn-on Mode Fluorescent Diarylethenes: Strategies for Controlling the Switching Response," *Bull. Chem. Soc. Jpn.* 2018, 91; pp. 237-250. Doi:10.1246/bcsj. 20170365.

J.F. Shida et al., "Low-dose high-resolution TOF-PET using ionization-activated multi-state low-Z detector media," *Nuclear Inst. and Methods in Physics Research, A* 1017 (2021) 165801; pp. 1-10.

Joao Francisco Shida et al., "Using Switchable Fluorescent Molecules to Image Track and Measure Energy of Double-Beta Decay Events in Large Liquid Detectors," The 2020 University of Chicago Undergraduate Research Symposium Proceedings: Abstract, PSCD Oral: Physical Science & Mathematics.

Eric Spieglan et al., "Using Switchable Fluorescent Molecules to Image Track and Measure Energy of Double-Beta Decay Events in Large Liquid Detectors," Presentation given at CPAD Instrumentation Frontier Workshop Dec. 9, 2019; pp. 1-23.

E. Angelico et al., "Capacitively coupled pickup in MCP-based photodetectors using a conductive metallic anode," Preprint submitted to Elsevier, Oct. 6, 2016; pp. 1-10.

Eric Oberla et al., "A 15 GSa/s, 1.5 GHz Bandwidth Waveform Digitizing ASIC," Preprint submitted to Elsevier, Sep. 18, 2013.

B.W. Adams et al., "Timing characteristics of Large Area Picosecond Photodetectors," *Nuclear Instruments and Methods in Physics Research A* 795 (2015); pp. 1-11.

The International Search Report and the Written Opinion issued on Feb. 25, 2022 for International Patent Application No. PCT/US2021/ 056535; pp. 1-12.

Suleman Surti et al., "Advances in time-of-flight PET," *Phys. Med.* (Jan. 2016); 32(1): 12-22. Doi: 10.1016/j.ejmp.2015.12.007.

S. Vandenberghe et al., "Recent developments in time-of-flight PET," *EJNMMI Physics* (2016) 3:3; pp. 1-30. DOI 10.1186/s40658-016-0138-3.

Dr. James E. Parks, "The Compton Effect—Compton Scattering and Gamma Ray Spectroscopy," Department of Physics and Astronomy, the University of Tennessee, Knoxville, Tennessee; revision 3.00 Jan. 6, 2015; pp. 1-37.

K. Karatasoulis et al., "Evaluation of Compton scattering sequence reconstruction algorithms for a portable position sensitive radioactivity detector based on pixelated Cd(Zn)Te crystals," arXiv preprint arXiv: 1011.2604 (2010); pp. 1-16.

Eric Oberla et al., "The design and performance of a prototype water Cherenkov optical time-projection chamber," *Nuclear Instruments and Methods in Physics Research A* 814 (2016) 19-32.

\* cited by examiner

Standard Jaszczak Phantom™
Model ECT/STD/P (Biodex 043-762)

For use with medium to high spatial resolution SPECT and PET systems.

Specifications:
Rod Height: 8.8 cm
Rod diameters: 6.4, 7.9, 9.5, 11.1, 12.7 and 19.1 mm
Solid sphere diameters: 12.7, 15.9, 19.1, 25.4, 31.8, and 38 mm
Interior diameter: 21.6 cm

POSITRON EMISSION TOMOGRAPHY SYSTEMS BASED ON IONIZATION-ACTIVATED ORGANIC FLUOR MOLECULES, PLANAR PIXELATED PHOTODETECTORS, OR BOTH

CROSS-REFERENCE TO RELATED APPLICATIONS

The present application is a National Stage of International Application No. PCT/US21/56535, filed Oct. 26, 2021, which claims priority to U.S. provisional patent application No. 63/106,665 that was filed Oct. 28, 2020, the entire contents of both of which are incorporated herein by reference.

BACKGROUND

Conventional positron emission tomography (PET) has unique capabilities in diagnostics. However, its use is limited by the large radiation dose to the patient, limited resolution, the cost of high-density crystal scintillators, and in many configurations a complicated mechanical construction.

Commercial PET detectors use high-density crystals as scintillators to lessen blurring due to the non-point-like nature of energy deposition by gamma-rays in the crystal. The crystal scintillators are expensive and the high cost has resulted in wide-spread use of scanner designs with reduced geometrical coverage. This forces a longer exposure during which a small-solid-angle scanner moves over the patient in multiple scans, resulting in a larger total radiation dose to the patient. The precision scanner mechanisms are expensive and need to be maintained. The longer exposure time may limit the through-put of the system, increasing the cost-per-patient.

In current PET detector designs, the spatial resolution on the gamma-ray interaction point is proportional to the size of the crystals. Measuring the distribution of light shared with neighboring crystals allows a resolution in the plane of the crystal array that is a fraction of the crystal size.

Time-of-flight PET (TOF-PET) supplies information on the position of a positron-electron annihilation along a line-of-response (LOR) by measuring the difference in times of arrival of each gamma-ray in a gamma-ray pair generated by the annihilation in two opposing crystals in a detector array. The typical time resolution of commercial TOF-PET scanners is 500 psec, corresponding to a spatial resolution of about 150 mm along the line-of-response (the gamma-gamma axis).

PET is currently limited to use in large hospitals and for a limited set of patients. For example, hairline fractures, which are common in falls of the elderly, can be difficult to diagnose with X-rays, but are highly visible in a PET scan. However, the preparation and large radiation dose dictate against the prescription of PET in such cases, and the less-effective X-ray diagnostic is instead widely prescribed instead of PET. The large radiation dose also limits the patient population that can be exposed and how often; for example, the use of PET for children is typically recommended only for extreme cases.

SUMMARY

Gamma-ray detection systems, including positron emission tomography (PET) and time-of-flight positron emission tomography (TOF-PET) systems, and methods for detecting gamma-rays and imaging samples using these systems are provided. The PET systems can be used in conventional patient imaging applications. In addition, because the PET systems can operate using low radiation doses and provide high image resolution, they can also be used to open new avenues for diagnosis and treatment. Examples include early detection of immune response to a pathogen, follow-up diagnosis after serological diagnosis of cancer, and real-time monitoring of hadron therapy.

One example of a positron emission tomography system includes a plurality of imaging modules, the imaging modules including: a scintillator compartment containing a low atomic number scintillating medium comprising one or more fluors, the scintillator compartment having a front face and a back face; a photodetector system comprising: one or more photodetectors optically coupled to the scintillator compartment and configured to detect scintillation photons generated in the scintillating medium; and one or more reflecting surfaces configured to reflect scintillation photons generated in the scintillating medium to the one or more photodetectors. The system further includes an optical imaging system that includes: one or more excitation light sources optically coupled to the scintillator compartment and configured to direct excitation light onto the scintillating medium; and one or more fluorescence detectors optically coupled to the scintillator compartment and configured to detect fluorescence generated by the fluors in the scintillating medium.

One example of a method for imaging a sample using a positron emission tomograph system of a type described herein, includes the steps of: positioning a sample within an imaging volume defined by the plurality of imaging modules, wherein positron-electron annihilation events in the sample generate coincident gamma-ray pairs; detecting coincident gamma-ray pairs arriving at a pair of imaging modules using the time-of-flight photodetector system by detecting scintillation photons generated when a first gamma-ray of a coincident gamma-ray pair interacts with the scintillating media in a first imaging module and a second gamma-ray of the coincident gamma-ray pair interacts with the scintillating medium in a second imaging module within a coincidence time window; initiating a sequence of steps for the first and second imaging modules of each pair of imaging modules that detects a coincident gamma-ray pair. The sequence of steps includes: triggering a recording of scintillation light by the time-of-flight photodetector system; interrogating the scintillating medium by directing excitation light from the one or more excitation light sources onto the scintillating medium, wherein the excitation light excites fluors that have been activated by ionization energy deposited in the scintillating medium by Compton electrons; recording fluorescence emitted by the excited fluors to generate images of energy clusters corresponding to Compton scatters of the first gamma ray in the scintillating medium of the first imaging module and images of energy clusters corresponding to Compton scatters of the second gamma-ray in the scintillating medium of the second imaging module; identifying the location of a first collision for the first gamma-ray in the scintillating medium of the first imaging module and the location of a first collision for the second gamma-ray in the scintillating medium of the second imaging module; and forming a line-of-response between the location of the first collision for the first gamma-ray and the location of the first collision for the second gamma-ray; and generating an image of a spatial distribution of the positron-electron annihilation events within the sample based on the lines-of-response.

Another example of a method for detecting gamma-rays uses a detection system including at least one imaging module having an associated imaging volume, the imaging module comprising: a scintillator compartment containing a low-atomic number scintillating medium; and a planar, pixelated photodetector optically coupled to the scintillator compartment and configured to detect scintillation photons generated in the scintillating medium. This method includes the steps of positioning a sample within the imaging volume, wherein the sample generates at least one gamma-ray from a gamma-ray source location, and further wherein the at least one gamma-ray undergoes a first Compton scatter in the scintillating medium of the at least one imaging module to generate a scintillation photon wavefront; and imaging the scintillation photon wavefront as a time-series of expanding rings of scintillation photons arriving at the planar, pixelated photodetector; and reconstructing a location and time of the first Compton scatter from the time-series of expanding rings of scintillation photons and the arrival-times of the scintillation photons at the planar, pixelated photodetector.

Other principal features and advantages of the invention will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings, wherein like numerals denote like elements.

DETAILED DESCRIPTION

Figure 1:
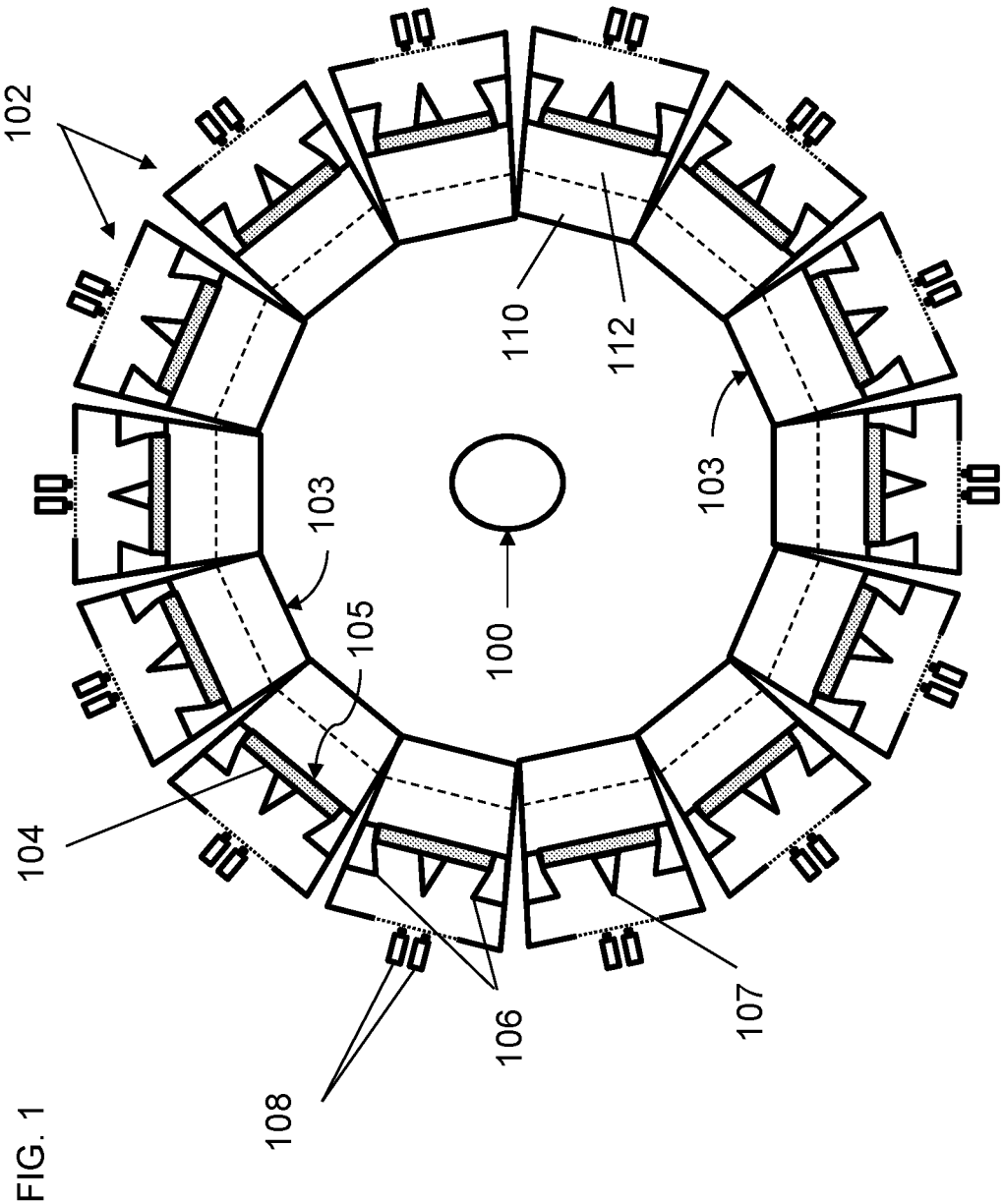
FIG. 1. A cross-sectional view of one implementation of a modular TOF-PET whole-body scanner based on Switchillators. A sample 100 is located in the center of a cylindrical array of imaging modules 102. During the operation of the scanner, each of the two gamma-rays 101 (gamma ray shown in FIG. 2) of a gamma-ray pair enters an imaging module through a front-side mirror acting as the entrance surface 103. A fast-timing photodetector (FT-photodetector) 104 is optically coupled through the back surface 105 of the Switchillator compartment. An optics system 106 that may include, for example, lens, mirrors, and/or a reflecting prism 107, controls the scanning and focus of twin lasers 108 in the active Switchillator volume 110. Digital cameras (not visible in this view, but visible in the perspective view in FIG. 3) have a wide-angle stereo view of the active Switchillator volume through the backside surface and a passive optical transition volume 112 that is optically matched to the active volume 110.

Gamma-ray detectors for the detection of one or more gamma-rays are provided. Also provided are methods of using the detectors for the detection of one or more gamma-rays. The detectors can be used in high-spatial resolution PET systems, including time-of-flight (TOF)-PET systems.

Some embodiments of the gamma-ray detectors utilize fluors and an optical imaging system to determine the time and location of a first scattering event of a gamma-ray in a low-density scintillating medium. These embodiments are referred to as Switchillator-based detectors and systems. Other embodiments of the gamma-ray detectors determine the time and location of a first scattering event of a gamma-ray in a low-density scintillating medium by imaging scintillation photons from the scattering event as a time-series of photon "rings" using a planar pixelated photodetector as a scintillation photon counter. These embodiments are referred to as ring-imaging scintillation counter-based detectors and systems. Optionally, both embodiments of the gamma-ray detectors can be combined in a single detector system.

The gamma-ray detectors and the PET systems can be used to study a gamma-ray emitting sample. For most applications, the gamma-rays will be emitted from the sample as a coincident gamma-ray pair that result from a positron-electron annihilation event in the sample, and the two coincident gamma-rays of the pair will be detected by different imaging modules. A line connecting the locations in the imaging modules at which the two gamma-rays are detected (referred to as a line-of-response (LOR)), within a coincident time window, together with the arrival times of the two gamma-rays can be used to identify the location of the gamma-ray source in the sample. However, the gamma-ray detectors can be used to detect the emission of single gamma-rays and/or gamma-rays that are not emitted as coincident pairs.

Switchillator-Based Detectors and Systems

PET systems that utilize the fluors are constructed from imaging modules that include: a scintillating medium that contains an ionization-activated fluorescent substance, referred to herein as a fluor; an optical imaging system; and a fast-timing (FT) photodetector system. The scintillating medium containing the fluorescent substance is referred to as a Switchillator. Using the PET systems, the path of a gamma-ray through the scintillating medium can be analyzed in detail and accurately reconstructed to provide improved PET imaging of the source of gamma-rays. The PET systems described here include TOF-PET systems. However, the PET systems can also be used with non-PET-TOF systems.

When a gamma-ray enters a Switchillator in an imaging module, it undergoes a series of successive scatters (also referred to scattering events) at discrete interaction locations. Through these interactions, the gamma-ray loses its energy to the scintillating medium. The scatters include Compton scatters (also referred to as Compton scattering events) in which the gamma-ray collides with an electron. The energy and angle of the scattered electron and gamma-ray in Compton scattering are constrained by Compton kinematics. At each scatter, prompt scintillation light is emitted and this prompt scintillation light is detected by the photodetector in a FT-photodetector system, which provides a coincident trigger for the optical imaging system. The FT-photodetector system may be a TOF system in which one or more (or all) of the photodetectors in the system is a TOF photodetector that is equipped with electronics for measuring the arrival times of the scintillation light at the photodetector. If the FT-photodetector system is a TOF system, the arrival times of the prompt scintillation photons are also used to determine the location of the source of the coincident gamma-rays along the LOR.

At each Compton scatter, the Compton scattered electron (also referred to as a recoil electron) deposits ionization energy along its track as it moves through the Switchillator. The deposited ionization energy activates the fluor molecules in the vicinity of the ionization, and the optical imaging subsystem is used to repeatedly excite the activated fluors and image the resulting fluorescence in order to reconstruct the recoil electron track.

From the distribution pattern and fluorescence intensity of the activated fluors, the earliest Compton scatter in a series of scatting events can be identified, the path of the gamma-ray through the Switchillator can be reconstructed, the starting point of the track of a Compton electron can be identified, and the energy deposited along the path of the gamma-ray and the tracks of the Compton electrons can be determined. This information can be used to improve the imaging of a gamma-ray source by identifying, with high resolution, the end-point of an LOR, which corresponds to the starting point of the track of the first Compton scattered electron in the Switchillator. By way of illustration, the precision of the end points of a LOR for a gamma-ray pair can be improved by identifying, on a statistical basis, the earliest detectable interaction point of a gamma-ray in the Switchillator with a resolution of 100 µm or better, including resolutions of 20 µm or better. The inherent high resolution of the technique allows a significant reduction in radiation dose for a patient relative to conventional PET imaging systems.

The imaging of the gamma-ray source can be further improved by identifying and rejecting background signal generated by coincident gamma-rays that have scattered in the sample prior to entering an imaging module or by other background signal-generating events.

The activated fluor molecules along the ionization path of a Compton electron are excited and imaged with high-resolution by the optical imaging system, which includes controllable excitation light sources and fluorescence detectors. The high-resolution images provide measurements of the energies and positions of gamma-ray Compton scatters using one or more cycles of fluor excitation and imaging. The optical imaging system can resolve each of the Compton scatters into an energy cluster, and the path of the gamma-ray in the Switchillator, including its earliest scatter, can be reconstructed, on a statistical basis, from the clusters. In particular, the following information can be reconstructed: the location and magnitude of the energy transferred to the fluor molecules; the directions of the scattered gamma-rays and Compton electrons; and the angular relations among the energy clusters associated with the Compton scatters, which are kinematically constrained by the Compton scattering equation. The angular relations among the energy clusters also provide information that can be used to reject background signal generated by gamma-rays that have undergone in-patient scattering.

The images obtained by the optical imaging system can be digitally recorded, enabling the use of advanced algorithms and techniques to determine the topology and number of activated fluor molecules for improved gamma-ray energy and annihilation location resolution and the rejection of background signal due to in-patient scattering or other background sources.

Switchillator-Based Pet System Components

An embodiment of a Switchillator PET system, in this case a modular whole-body TOF-PET scanner, is shown schematically in FIG. 1. The system includes a plurality of imaging modules 102 arranged around a sample 100, here a human patient (the cross-section of the patient's head is represented by an oval). Although FIG. 1 shows a PET system implemented in a whole-body TOF-PET system, it should be understood that the PET systems need not be part of a whole-body TOF-PET system.

The PET system may include a sample holder configured to position the sample 100 centrally within the imaging volume defined by the one or more imaging modules. As used herein, the term "imaging volume" refers to a location at which a sample can be placed, such that gamma-rays being emitted from the sample are able to be enter the scintillating media in the scintillator compartments. In some embodiments, the sample holder is a horizontal platform, such as a table or bed, or a vertical surface against which the sample is placed. Samples to be imaged with PET systems include humans and non-humans, such as other animals, plants, and inanimate materials.

For whole-body imaging, the imaging modules 102 may be arranged in a cylindrical geometry (to define a cylindrical imaging volume) around the sample as in a conventional PET detector, as illustrated in FIG. 1, or arranged in a moveable rectangular geometry for patient comfort, as described in U.S. Pat. No. 10,132,942, or arranged in a custom geometry for specialized applications. Alternatively, multi-module arrays of the modules can be configured to optimize for differing body sizes and mobility issues. For specialized imaging of smaller samples, such as the brain or extremities, or for example, small animal imaging, application-specific modules can be in a suitably-designed fixed or configurable geometry.

Figure 2:
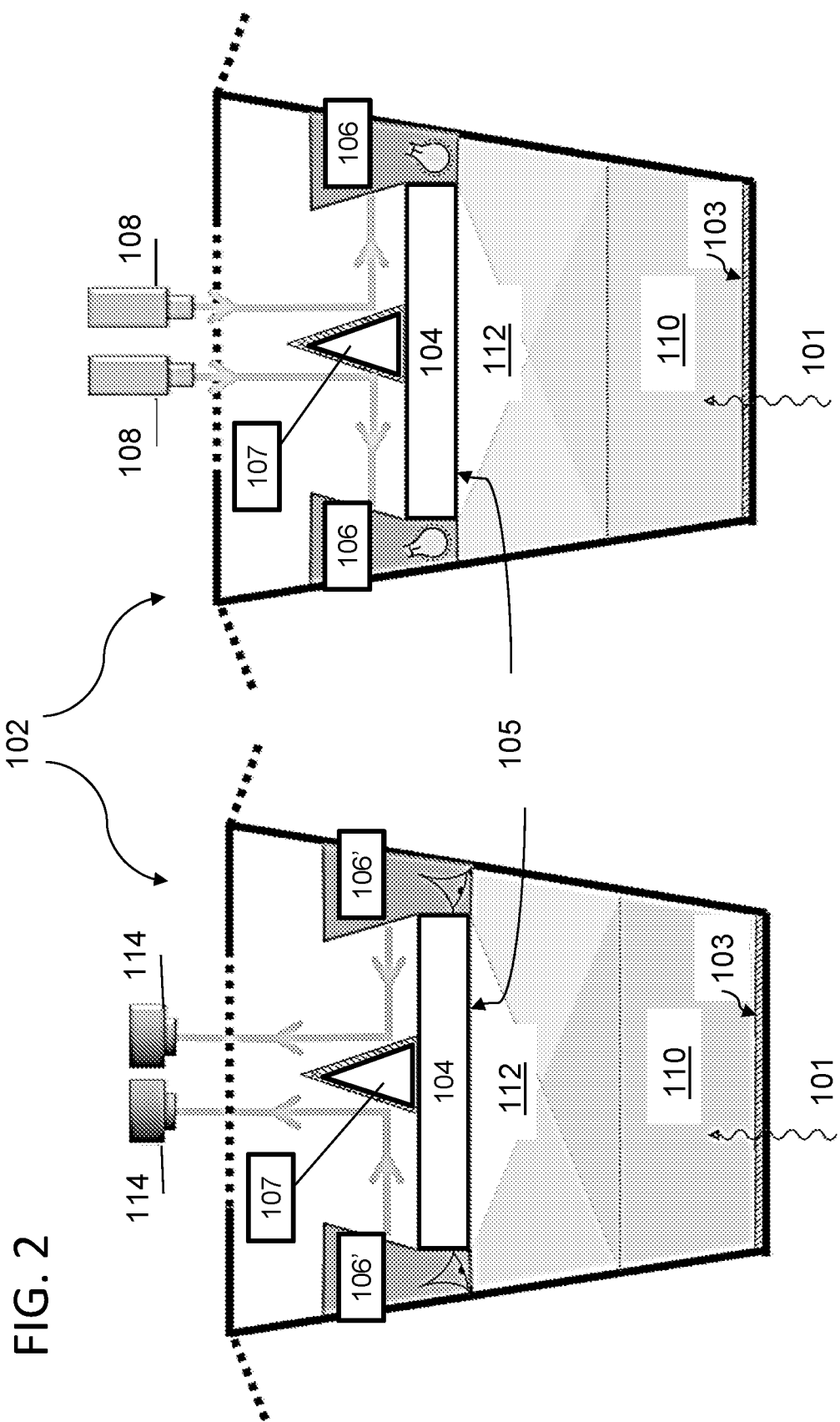
FIG. 2. Plan view of an example implementation of a single imaging module 102 for a cylindrical TOF-PET whole-body scanner, such as shown in FIG. 1. The right panel shows a cross-sectional view taken through a plane bisecting lasers 108, as shown in FIG. 1. The left panel shows cross-sectional view of the same module rotated 90°, where the cross-section is taken through a plane bisecting digital cameras 114. The sample is located below the module; the gamma-rays 101 enter the Switchillator volume 110 through a front window and mirror 103. The digital cameras 114 and the lasers 108 view the active Switchillator volume 110 through transition volume 112. The left-hand panel shows the digital camera subsystem comprising the cameras 114, the camera optic components 106' and a reflecting prism 106. The right-hand panel shows the same module rotated by 90 degrees to display the twin laser subsystem comprising the lasers 108, the laser optic components 106 with reflecting prism 107.
Figure 3:
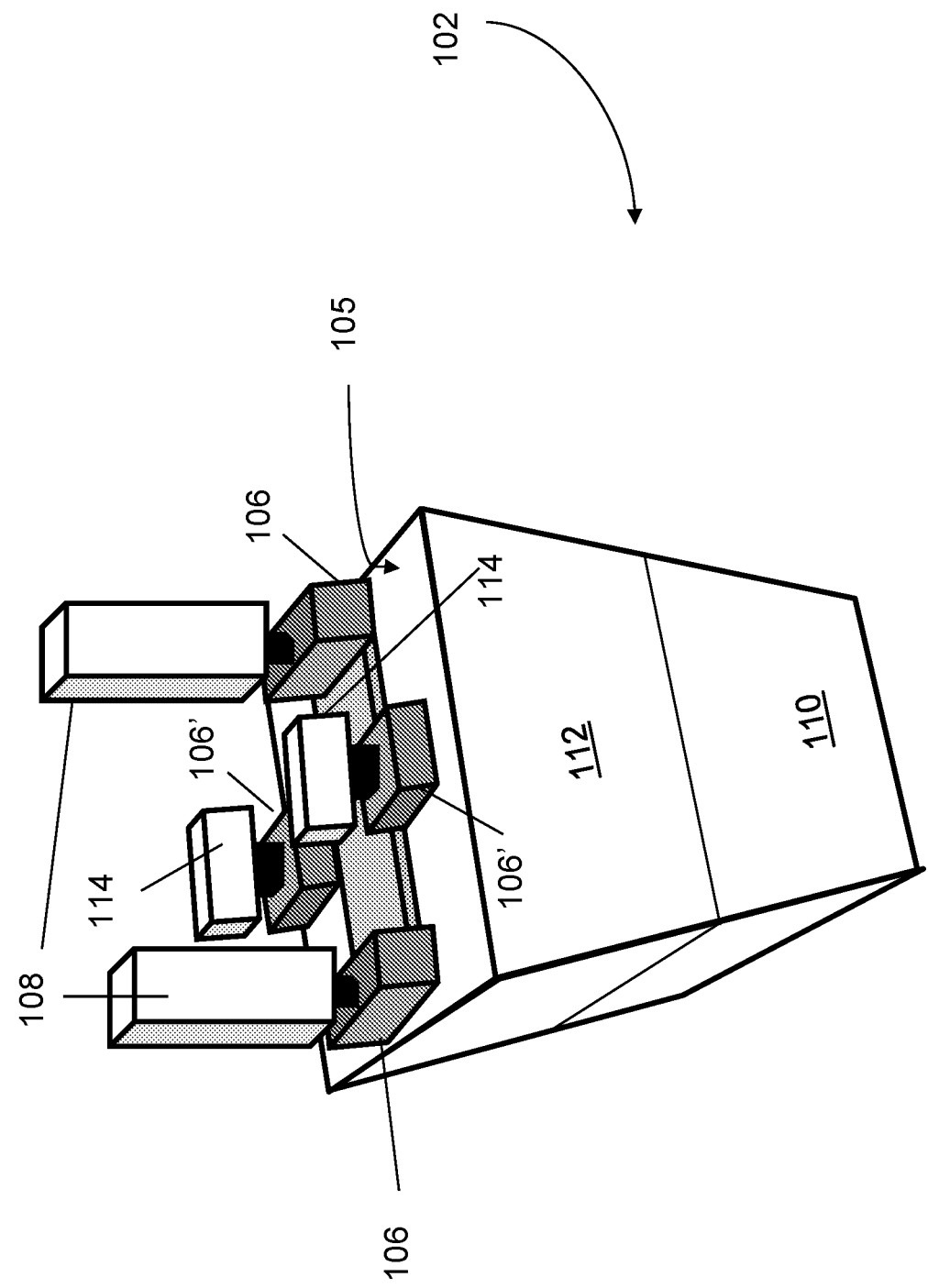
FIG. 3. A 3D view of an example implementation of a single imaging module 102 for a cylindrical TOF PET whole-body scanner, such as shown in FIG. 1 and FIG. 2. The sample is located below the module. The gamma-ray encounters, in sequence, the entrance surface which is mirrored 103 on the inside, the active scintillator volume 110, and, optionally, the optically matched transition volume 112 that does not contain fluor molecules. The FT-photodetector 104 is optically coupled to the transparent backside surface 105 of the Switchillator compartment. An optics subsystem 106 controls the scanning and focus of twin diode lasers 108 in the active Switchillator volume 110. (For simplicity, reflecting prism 107 is omitted from this view.) The twin diode lasers 108 illuminate the Switchillator volume 110/112 through the backside surface 105 around the FT-photodetector 104.

Plan and three-dimensional views of an exemplary imaging module are shown in FIG. 2 and FIG. 3, respectively. Each imaging module includes a scintillator compartment containing a fluor-containing scintillating medium 110. The entire volume of the scintillating medium may include the fluor molecules, or the volume of scintillating medium may include a sub-volume 112 that includes fluor molecules (referred to here as an active volume) and a sub-volume that does not include the fluor molecules 110. Gamma-rays 101 from positron-electron annihilations in the sample 100 enter the active volume 110 of the scintillating medium through the imaging module surface facing the sample (front surface) 103.

Each imaging module includes an FT-photodetector system that includes a fast-timing photodetector 104 optically coupled to the scintillator compartment. As used here, the term "optically coupled" means that the photodetectors are positioned such that scintillation photons from the scintillating medium can reach and be detected by the photodetectors. The photodetectors detect the scintillation light produced by the first and subsequent gamma-ray scattering events within the Switchillator. As used herein, the term "FT-photodetector" or "fast timing photodetector" refers to a photodetector having a timing resolution that is sufficiently fast to resolve different scattering events in a series of successive scattering events generated when a gamma-ray interacts with the scintillating medium. Thus, the FT-photodetectors are characterized in that their temporal resolutions are equal to or better than the temporal separation of the scattering events in the scintillating medium.

As shown in the embodiment of FIGS. 2 and 3, the FT-photodetectors 104 may be mounted on the back 105 of the Switchillator compartments. The FT-photodetector system may also include electronic controls and readout systems and optical components such as mirrors, lenses, prisms, apertures, and/or baffles. Readout systems having high sampling rates—for example, sampling rates of at least 5 GS/s—are desirable. The difference between the calculated times-of-arrival of the gamma-rays of a coincident pair by the FT-photodetector systems of two imaging modules is used to calculate the position of the annihilation event in the sample being imaged along an LOR with an associated uncertainty distribution. In this example implementation, the internal surface of the Switchillator compartment front face has been made reflective to roughly locate energy depositions (scatters) and to improve the arrival time resolution by measuring the difference in scintillation light transit times to the front 103 and back 105 surfaces of the Switchillator compartment.

In addition to measuring the arrival times of prompt scintillation photons, the FT-photodetector system provides a coincidence trigger for the optical imaging system to initiate a sequence of repeated fluor excitation and fluorescence imaging cycles. If the scintillating medium is a low atomic number material that enables the resolution of the timing and location of energy depositions associated with discrete Compton scatters, the fast photodetectors 104 can also provide preliminary information about the locations of the energy clusters associated with the Compton scatters in the Switchillator for optical imaging. Such low atomic number (which are also low-density) scintillator materials are described in U.S. Pat. No. 10,132,942. Conversely, the time-ordered map of energy clusters and the gamma-ray trajectory reconstructed using the Switchillator can be used to refine the timing and location information from the TOF photodetector system to further refine the LOR end point identification and probability distribution for an annihilation event along the LOR.

Candidates for the photodetectors 104 used in the FT-photodetector system include, but are not limited to, solid-state photodetectors such as silicon photomultipliers and vacuum-based photomultiplier tubes (PMTs), including MCP-PMTs. In the example implementation of FIGS. 2 and 3, a large-area flat-panel MCP-PMT such as a large-area, flat-panel photodetector (LAPPD) is mounted on the back surface 105 of the Switchillator compartment, and the front surface of the Switchillator is mirrored 103 to be reflective. Suitable PET systems with TOF capabilities are described in U.S. Pat. No. 8,604,440. However, other suitable photodetector systems with TOF capabilities are known and commercially available.

Each imaging module also has an optical imaging system that includes at least one light source for exciting activated fluor molecules and at least one fluorescence detector for detecting fluorescence emitted by the excited fluor molecules. The imaging modules 102 may further include optical components 106/106'/107, electronic circuitry, and data acquisition and analysis systems for generating and displaying digital images. The example implementation of an optical imaging system shown in FIGS. 2 and 3 incorporates dual laser diodes 108 as excitation light sources and dual digital cameras 114 as fluorescence detectors. The light sources and fluorescence detectors are optically coupled to the scintillator compartment and the Switchillator contained therein, meaning that the light sources are positioned such that light from the light sources can be directed onto the Switchillator, either directly or with the use of an optics system, and that the fluorescence detectors are positioned such that fluorescence emitted by the fluors in the Switchillator can be imaged by the fluorescence detectors, either directly or with the use of an optics system. In the embodiment of FIGS. 2 and 3, the laser diodes and digital cameras are mounted on the back surface of the Switchillator compartment, and the excitation light provided by the twin diode lasers 108 is steered and focused in the horizontal and vertical planes by an optics system 106/107 composed of controllable mirrors and lenses to provide wide-angle stereo coverage of the entire Switchillator volume. The cameras 114 can also be steered and focused in the horizontal and vertical planes by an optics system 106'/107 composed of controllable mirrors and lenses to provide wide-angle stereo viewing of the entire Switchillator volume 110/112.

Optionally, to facilitate full coverage with wide-angle stereo viewing, an optical transition region 112 may be employed between the active Switchillator volume 110 and the back face 105 of the Switchillator compartment. In FIGS. 2 and 3, the transition region is a passive volume containing a transparent fluor-free liquid having an index of refraction that matches the index of refraction of the Switchillator. Alternative geometries may include more sophisticated optical interfaces and optical components.

The optical imaging system may further include electronic controls and readout systems and optical components such as mirrors, lenses, prisms, apertures, and/or baffles that allow the beam of excitation light to be shaped, focused, pulsed, and/or scanned over the active Switchillator volume, and to synchronize the beam of excitation light with the fluorescence detectors.

In the example imaging module of FIGS. 2 and 3, electronics used to support control, data acquisition, calibration, and local data analysis, including a complete imaging of the gamma-ray trajectory in the Switchillator, can also be mounted on the back surface of the Switchillator compartment.

Switchillator Composition

The Switchillator comprises two components. The first component absorbs ionizing energy from a gamma-ray and emits scintillation light, typically visible or ultraviolet light. The second component is fluors that are activated by the deposited ionizing energy and excited by the excitation light sources. The component of the scintillating medium that absorbs ionizing radiation from the gamma-ray and emits prompt scintillation light can also be considered a type of fluor, but it is distinguishable from the fluors that are imaged using the optical imaging system. Because the scintillation light emitting fluors ("scintillation fluors") and the fluor molecules imaged by the optical imaging system ("Switchillator fluors") are distinct, the scintillation fluors can be chosen to optimize speed and yield for TOF resolution independent from the choice of the Switchillator fluors. Other components that may be included in the Switchillator include substances that enhance energy transfer from the ionization to the fluors.

The scintillating medium has a low average atomic number. As used herein, a scintillating medium having a low atomic number is a scintillating medium that permits successive gamma-ray scattering events, such as successive Compton scatters, in the medium to be sufficiently separated in space and time that the individual scattering events can be resolved by the FT-photodetector. Thus, the requirements for the FT-photodetectors and the low atomic number scintillating media are interrelated: a lower atomic number scintillating medium lowers the timing resolution requirements for the FT-photodetector, while a faster photodetector may enable the use of a higher atomic number components in the scintillating medium. Liquid scintillating media and gas scintillating media fall within the category of low atomic number scintillating media, where the term liquid—as used herein—includes viscous fluids, such as gels. However, a low atomic number scintillating medium can also be a solid crystal, provided the solid material has a sufficiently low average atomic number to allow for adequate spatial and temporal separation of successive scattering events in the crystal. Water-based and organic solvent-based liquid scintillators are examples of low atomic number scintillation media that can be used.

Suitable fluors include organic molecules, such as diarylethenes. Examples of diarylethene Switchillators fluors that can be used in the PET systems are diaryethenes, as described in Kakishi Uno et al. *Journal of the American Chemical Society* 133.34 (2011), pp. 13558-13564; Masahiro Irie et al., *Bulletin of the Chemical Society of Japan* 91.2 (2017), pp. 237-250; Dojin Kim et al., *Advanced Functional Materials* 28.7 (2018), p. 1706213; and Ryota Kashihara et al., *Journal of the American Chemical Society* 139.46 (2017), pp. 16498-16501.

Fluors can be incorporated into a scintillating medium by, for example, dissolving them in a solvent of a liquid scintillator. Suitable solvents include, but are not limited to, aromatic organic solvents such as toluene, xylene, dodecyl benzene, diisopropyl naphthalene, phenyl xylyl ethane, and mixtures thereof. The Switchillator fluors can be incorporated into a solid scintillating medium using the same processes that are currently used to incorporate conventional scintillation fluors into a solid medium.

The Switchillator fluors respond to the deposition of energy into the Switchillator by switching from an inactive ("OFF") state to an active ("ON") state. For example, the Switchillator fluors may be activated by ionization from the ground state to a quasi-stable fluorescent state. One process of converting a fluor molecule from an inactive state to an active state is explained as follows. When an ionizing particle, in this case a Compton electron scattered by a gamma-ray, deposits ionizing energy in the solvent of a liquid scintillating medium, excited states are produced in the solvent molecules. These excited states in turn transfer their excitation energy to the fluor molecules, converting them from an OFF state that neither strongly absorbs visible light nor fluoresces, to an ON state that absorbs visible light and fluoresces with high efficiency. The switching of the fluors from their OFF state to their ON state is referred to as activating the fluors. Once activated, the fluors can be excited by the excitation light source of the optical imaging system and the resulting fluorescence can be recorded to produce an image. The activated fluors can be repeatedly excited by the excitation light source in order to extract multiple photons before either reverting to their inactive state, either by a mechanism that is inherent in the material or excitation process, or by being reset using an external mechanism.

Pet Imaging Using Switchillators

The positions, patterns, and amount of energy deposited by the Compton scatters as a gamma-ray travels on a path through the Switchillator are reconstructed by imaging the fluorescence emitted by the activated fluor molecules. A detailed description of illustrative algorithms and processing steps that can be used to carry out such reconstruction is provided in Example 2. A brief description of steps that can be used to carry out such reconstruction and to use the reconstruction to improve PET imaging of a gamma-ray source are described briefly here.

When the optical imaging system is triggered by the FT-photodetector system, the fluorescence detectors (e.g., diode lasers) excite activated fluors and the resulting fluorescence is imaged, repeatedly, by the photodetectors. Compton scatters in the Switchillator show up as fluorescing pixels in the image. Clusters of the fluorescing pixels (energy clusters) are identified, wherein each energy cluster is associated with an energy deposition event (Compton scatter) along the path of the gamma-ray in the Switchillator. The pixels in the image can be assigned a statistical weight corresponding to the intensity (brightness) of the background-subtracted fluorescence.

A statistical significance can then be assigned to each energy cluster based on the product of the statistical significance values for all of the pixels that make up the energy cluster, such that energy clusters with a greater overall fluorescence intensity are assigned a higher statistical significance. The intensity of the fluorescence is proportional to the number of activated fluor molecules, which is proportional to the deposited ionization energy, with a conversion factor that can be more than $10^4$ molecules per MeV. Because the earliest Compton scatters will generally transfer more ionizing energy into the scintillating medium, the energy clusters with a higher statistical significance (i.e., the energy clusters with the highest overall brightness) are more likely to correspond to the earliest Compton scatter and, therefore, an identification of the earliest Compton scatter can be made based on the fluorescence image.

Imaging the energy clusters at a higher resolution allows the tracks of the Compton scattered electrons along the trajectory of the gamma-ray to be resolved and recorded based on the location and number of the activated fluor molecules that are imaged. The starting point of the first Compton scattered electron track can be determined on a statistical basis from the evolution of ionization and scattering along the track. In typical solvents, the fluor molecules remain within about 10 μm of the point of the energy transfer for many milliseconds, enabling high resolution imaging of the individual Compton electrons from successive Compton scatters in the Switchillator.

The information about the locations of the Compton scatters, the energy deposited by the Compton scatters, and the direction of the Compton recoil electrons and scattered gamma-rays, in combination with the constraints placed on the system by Compton kinematics, can be used to recreate the trajectory of the gamma-ray in the Switchillator, to identify the Compton scatter that is most likely to be the earliest Compton scatter, and to identify the starting point of the Compton electron track for the earliest Compton scatter, which corresponds to the location of the first collision of the gamma-ray with an electron. This information can, in turn, be used to identify, with high resolution, the end point of an LOR for a coincident gamma-ray pair and to identify and reject false coincidences and other background signals. Background signals from random coincidences, in-patient scatters, and other spurious signal-generating events can be rejected more completely using the full kinematic information of the gamma-ray interactions provided by the PET systems described herein than by the conventional simple energy cut.

The many-dimensional parameter space provided by the PET systems described herein lends itself to sophisticated multi-variable analysis methods, including machine learning, event-by-event optimization, and adaptive weighting. Additionally, the methods lend themselves to implementation in real time.

Ring-Imaging Scintillation Counter-Based Detectors and Systems

Gamma-ray detectors that determine the time and location of a first scattering event of a gamma-ray in a low-density scintillating medium by imaging scintillation photons in a time-series of scintillation photon rings (RISC-based detectors) include one or more imaging modules containing a low-density scintillating medium in a scintillation compartment and a planar, pixelated FT-photodetector optically coupled to the scintillator compartment and configured to detect scintillation photons generated in the scintillating medium.

Figure 20:
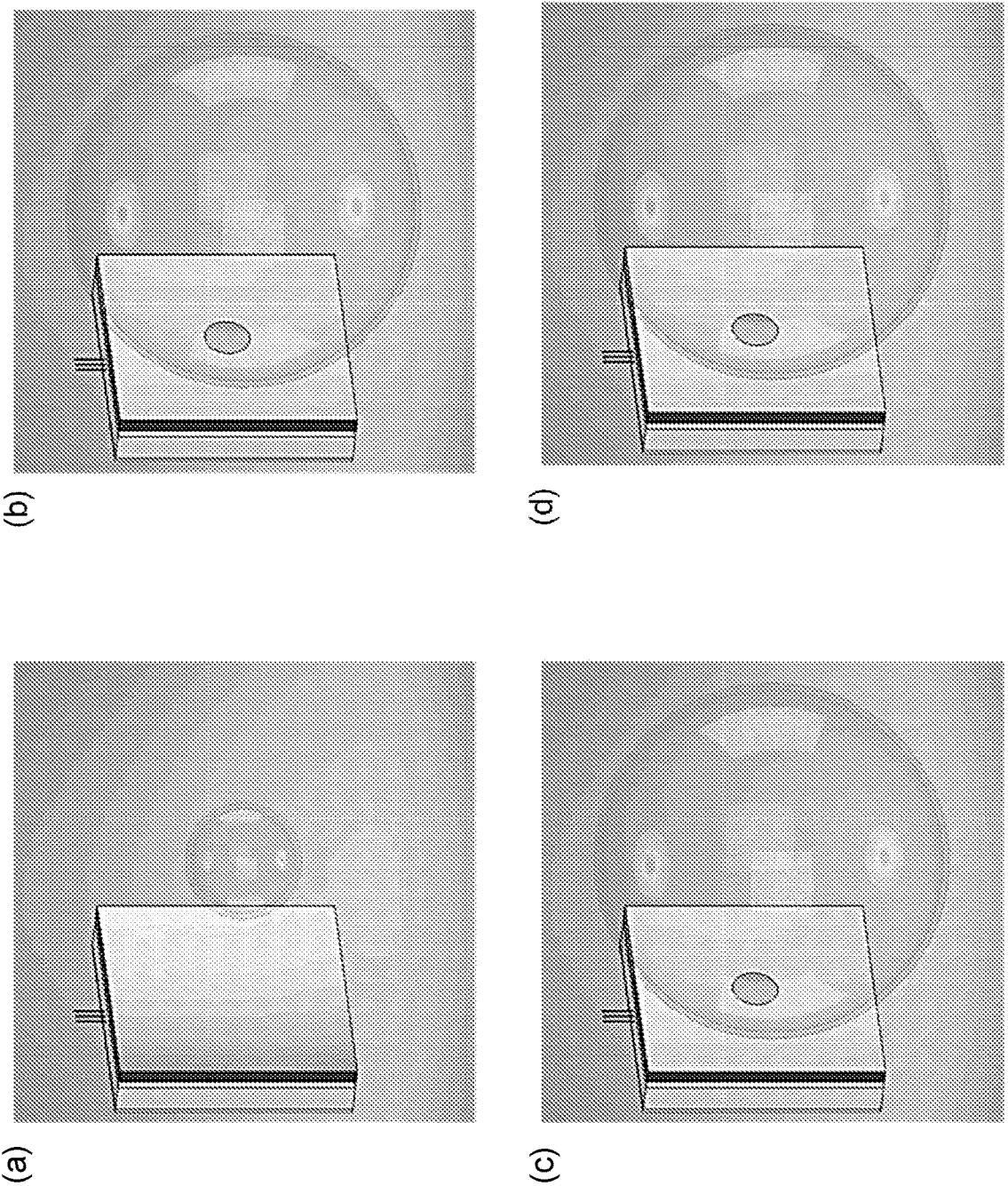
FIG. 20, panels (a) through (d), is a schematic illustration of RISC-based gamma-ray detection. For simplicity, the pixelation of the photodetector is not delineated in the figure.

RISC-based gamma-ray detection is illustrated schematically in FIG. 20, panels (a)-(d). When a gamma-ray from a gamma-ray emitting sample enters the scintillation medium, it undergoes at least one scattering event, such as a Compton scatter, at a discrete interaction location. As a result of the scattering event, prompt scintillation photons are emitted isotropically and, therefore, form an expanding spherical scintillation photon wavefront 200 (FIG. 20, panel (a)). When the expanding wavefront 200 initially impinges on a front face of the planar, pixelated photodetector 201, the individual scintillation photons may initially form a roughly circular pattern 202 (FIG. 20, panel (b)) on the pixel of planar, pixelated photodetector 201. As scintillation wavefront 200 expands, the scintillation photons impinging on the front face of planar, pixelated photodetector 201 form a ring-shaped pattern 203 in which the diameter of the ring expands over time (FIG. 20, panels (c) and (d)). As illustrated in FIG. 20, panels (a)-(d), by detecting the photons impingent upon planar, pixelated, photodetector 201 at different times, the scintillation photon wavefront 200 can be imaged as a time-series of expanding rings.

Based on the dimensions of the rings in the time-series of images, the location of the center of the expanding spherical scintillation photon wavefront, which corresponds to the location of the scattering event giving rise to the wavefront, can be determined. Moreover, the time of the said scattering event can be determined based on the arrival times of the scintillation photons at the planar, pixelated photodetector and the speed of the scintillation photons in the scintillating medium, which will be determined by the index of refraction of the scintillating medium. Thus, RISC-based detectors can be used to reconstruct the location and time of a scattering event, such as a Compton scatter, within the scintillating medium.

Notably, RISC-based detection can be used to reconstruct the time and location of an initial scattering event, as well as subsequent scattering events in a series of successive scattering events. This is illustrated in FIG. 20, panel (d), which shows the earliest scintillation photons 204 from a subsequent scattering event arriving at the front face of planar, pixelated photodetector.

The RISC-based gamma-ray detectors and PET systems can use the same photodetector system components that are described above with respect to the Switchillator-based gamma-ray detectors and PET systems. However, the components of the optical imaging system will generally not be included in the RISC-based detectors and PET systems, unless RISC-based and Switchillator-based gamma-ray detection are being combined into a single system. Candidates for the planar, pixelated photodetectors of the RISC-based gamma-ray detectors and PET systems include, but are not limited to, planar arrays of solid-state photodetectors such as silicon photomultipliers and vacuum-based photomultiplier tubes (PMTs), including MCP-PMTs. Planar large-area flat-panel MCP-PMTs, such as a large-area, flat-panel photodetectors, as described in U.S. Pat. No. 8,604,440, may be used as the planar, pixelated photodetector. Additionally, the photodetector system may include high-speed multi-channel circuitry that allows for time-slicing the photodetector signals at fast intervals-for example, intervals of at least 10 GS/sec, including intervals in the range of 10-15 GS/sec.

The scintillator compartments and low-density scintillating media described above with respect to the Switchillator-based gamma-ray detectors and PET systems also may be used as the scintillating media in the ring-imaging scintillation counter (RISC)-based detectors and PET systems. However, the fluors will generally not be included in the scintillating media for the RISC-based detectors and PET systems, unless RISC-based and Switchillator-based gamma-ray detection is being combined into a single system. Scintillators with high light-output and fast rise and fall-times are preferred.

Like the Switchillator-based gamma-ray detectors and PET systems, the RISC-based gamma-ray detectors and PET systems may include a sample holder configured to position a sample centrally within the imaging volume defined by the one or more imaging modules. Samples to be imaged with RISC-based detectors and systems include humans and non-humans. For whole-body imaging, the imaging modules may be arranged in a cylindrical geometry around the sample as in a conventional PET detector or arranged in a moveable rectangular geometry for patient comfort, or arranged in a custom geometry for specialized applications.

The FT-photodetector system for the RISC-based detectors may be a TOF system in which one or more (or all) of the photodetectors in the system is a TOF photodetector that is equipped with electronics for measuring the arrival times of the scintillation light at the photodetector. If the FT-photodetector system is a TOF system and the gamma-rays being detected are coincident pairs, the timing and location information about the earliest scattering event can be used to determine with high accuracy the location of the source of the coincident gamma-rays along the LOR.

Example Applications

One application of low-dosage, high resolution PET systems described herein is the early detection of localized immune response to a pathogen before structural changes, such as early detection of immune system activity in the lungs or extremities of a patient in the case of a respiratory disease such as Covid-19.

The system is also useful for total-body screening studies, including those to characterize inflammation or immune response throughout the body. There have been significant reports to develop novel radio tracers for these applications and they would be well matched to the capabilities of the PET systems described here. (Singh, et al., in *The quarterly journal of nuclear medicine and molecular imaging: official publication of the Italian Association of Nuclear Medicine (AIMN)* [*and*] *the International Association of Radiopharmacology (TAR)*, [*and*] *Section of the Society* 54.3 (June 2010), pp. 281-290; and Wu et al., *Theranostics* 3.7 (2013).

Another application is the follow-up diagnosis of the serological diagnosis of cancer. An ultra-low dose whole-body scan would provide images for detecting metastasis. Blood tests have been developed which are able to detect signs of cancer in a wide range of organs through identification of mutated DNA or protein biomarkers circulating in the blood. Such assays would be minimally invasive and inexpensive. They could detect cancers earlier than any other screening test. However, blood tests provide little or no information about the location of tumors, so follow-up imaging would be needed to localize, size, and stage any detected cancer and potential metastases. A recent study showed the value of using conventional PET to follow up on positive results from a blood-based cancer screening assay. (Lennon et al., Science 369.6499 (July 2020).) The proposed low-cost, total-body, low-dose PET system described here would allow for high-throughput screening of the entire body in any patient with a positive blood test result.

Hadron therapy, in which the positron is created by a proton, pion, or neutron, is an application requiring a real-time accurate counting of positron annihilation events at high spatial and energy resolution to monitor the hadron beam and dose.

EXAMPLES

Example 1. Switchillator Design

This example provides illustrative guidance with respect to the selection of Switchillator fluors, using aromatic organic solvent-based scintillating media as examples. The primary considerations in selecting the fluors and designing a Switchillator are achieving high activation yields and low background levels.

Activation Yield:

High activation yield for a fluor solute requires efficient energy transfer from the excited states of the solvent to the fluors. When an ionizing particle traverses an aromatic organic solvent the products that survive after 1 ns are mostly low-lying singlet and triplet excited states of the solvent. The singlet states drive conventional scintillation emission by the Förster resonance energy transfer (FRET) mechanism. Both the singlet and triplet states may activate the fluor molecules for subsequent optical excitation. This activation may take the form of converting a non-fluorescent isomer of the fluor (inactive isomer) into a fluorescent isomer (active isomer).

By way of illustration, in toluene there are initially $1.35 \times 10^4$ singlet excitations per MeV from 10 MeV electrons. (JH Baxendale et al., Journal of the Chemical Society, Faraday Transactions 1: Physical Chemistry in Condensed Phases 69 (1973), pp. 771-775.) To achieve a 1% energy resolution at 511 KeV requires 20,000 activated Switchillator fluor molecules per MeV. A process using only singlet excitations of the solvent with an efficiency of 0.4 would provide an energy resolution of $\approx 1.5\%$. In comparison, there are $2.8 \times 10^4$ triplet excitations per MeV; a process able to use both triplet and singlet excitations at an efficiency of 0.4 would achieve an energy resolution of 0.8% at 511 KeV deposited.

A higher efficiency may be achieved by exploiting alternative mechanisms of activation of the Switchillator fluor. Examples include: 1) the use of a solvent with enhanced triplet excitations; 2) the use of water-based Switchillators with radical-mediated energy transfer; and 3) radical-mediated energy transfers in other solvents.

Signal-to-Background Ratio. The fluorescence signal from fluors activated by the gamma-ray is viewed against an intrinsic background signal from fluors activated by the excitation light source. Activation is controlled by: 1) the absorption cross-section of the OFF state of the fluor at the excitation wavelength, $\varepsilon_{OFF}((\lambda_{ex})$; 2) the quantum efficiency of switching from the OFF state to the ON state, $\Phi_{OFF \to ON}$; 3) the concentration $C_{OFF}$ of inactive (OFF) isomers of the fluor; and 4) the volume V being viewed.

If the Switchillator is predominately in the OFF state when illumination begins, the appropriate figure of merit is $Z_{dye}$, the ratio of background resulting from the activation of fluors by the excitation light source to signal from fluors activated by the ionization:

$$Z_{dye} = \frac{\varepsilon_{OFF}\Phi_{OFF \to ON}}{\varepsilon_{ON}\Phi_{ON;fl}} \quad (1)$$

$Z_{dye}$ is proportional to the ratio of active to inactive fluors in a readout voxel that can be successfully interrogated given some significance threshold. A smaller $Z_{dye}$ allows the use of larger voxels containing more of the uniformly distributed fluors. Conversely, a larger $Z_{dye}$ is permissible if $C_{OFF}$ can be made smaller while maintaining the activation yield by more efficient energy transfer from solvent to solute.

The Switchillator fluors can be activated by multiple mechanisms, including the excitation light source, previous ionizing gamma-ray interactions, and background ionization. A mechanism for deactivation of activated fluor molecules is consequently usually needed to maintain a stable signal-to-background contrast. Deactivation mechanisms include, but are not limited to, passive deactivation with an appropriate ON state lifetime, active deactivation by optical means, and the inclusion of a deactivating agent. An adequate deactivation lifetime may be achieved by modification of the fluor, the solvent, and/or the Switchillator composition.

In the case that the only resetting mechanism for the fluor is a reverse isomerization process with quantum efficiency $\Phi_{ON \to OFF}$ from the ON state, continuous illumination by the excitation light source results in a photo-stationary mixture:

$$\frac{C_{ON}}{C_{OFF}} = \frac{\Phi_{OFF \to ON}\varepsilon_{OFF}(\lambda_{ex})}{\Phi_{ON \to OFF}\varepsilon_{ON}(\lambda_{ex})} \quad (2)$$

Since each active fluor molecule typically emits $\approx >50$ photons, for useful Switchillator fluors $\Phi_{ON \to OFF}$ is small, and consequently $$\frac{C_{ON}}{C_{OFF}} \gg Z_{dye}.$$

Fluors which must be deactivated by light have a more demanding requirement on the absorption ratio between active and inactive forms.

The absorption cross-section at long wavelengths for the OFF state must be sufficiently small to limit activation at the excitation wavelength. The absorption bands of various fluorescent dyes in solution have a thermal tail at long wavelengths, the Urbach Tail, that falls approximately exponentially The exponential slope coefficient, defined as $\sigma$, is called the Urbach steepness coefficient. The absorption cross-section for excitation light of the OFF isomer, $\varepsilon_{OFF}$ ($\lambda_{ex}$) is determined by the product of the slope and the separation of the activation and excitation wavelengths, $\sigma(E_0-E_{ex})$, where $E_{ex}$ is the energy of the fluorescence excitation light. In the case of multiple exponential tails the cross-section will be dominated by the one with the slowest fall-off.

Illustrative Switchillator Specifications. The parameters, associated symbols, and desired values for a fluor molecule appropriate for a whole-body PET scanner are presented in Table 1 for the case of energy transfer by singlet excitations of the solvent. The parameter sets and values for different fluors, energy transfer mechanisms, and applications may differ.

TABLE 1

Example properties and values for Switchillator fluor molecules appropriate for a Switchillator-based PET system.

| # | Parameter | Symbol | Value | Comment |
|---|---|---|---|---|
| 1 | Activation Yield | $Y_{act}$ | $>5 \times 10^3$ | # of ON fluors per MeV deposited |
| 2 | Activation Wavelength | $\Lambda_{act}$ | <400 nm | Peak OFF to ON wavelength |
| 3 | Excitation Wavelength | $\Lambda_{ex}$ | 350-650 nm | At max separation |
| 4 | Dye Ratio | $Z_{dye}$ | $<10^{-10}$ | Ratio of background activation rate to fluorescence rate at $\lambda_{ex}$, $\dfrac{\varepsilon_{OFF}\Phi_{OFF \to ON}}{\varepsilon_{ON}\Phi_{ON;fl}}$ |
| 5 | On-State Lifetime | $\tau ON$ | $3 \times 10^{-7} - 10^2$ s | 1/e Lifetime of ON fluors in the dark |
| 6 | Fluorescence brightness | $\varepsilon_{ON}\Phi_{ON;fl}$ | $>10^3$/(M cm) | Rate of emission from active dye |
| 7 | Mean Absorption Length | $\chi(\lambda_{ex})$ | >6 m | 1/e absorption length of EL in detector at wavelength $\lambda_{ex}$ |
| 8 | Signal-to-Noise significance | Rs | 5 σ | Event Significance: product of pixel significances |
| 9 | Wavelength of FL | $\Lambda_{fl}$ | 400-700 nm | Wavelength of Fluorescence light |
| 10 | # of photons per activated Fluor | $N_{fl}$ | >50 | Mean # of fluorescent photons that can be extracted from an ON fluor before it deactivates |

Example 2. Image Acquisition, Processing, and Analysis

This example illustrates methods for acquiring, processing, and analyzing fluorescent images provided by a Switchillator-based PET system. The methods described here are for illustrative purposes only. Other method steps, parameters, and/or algorithms can be used.

Figure 4:
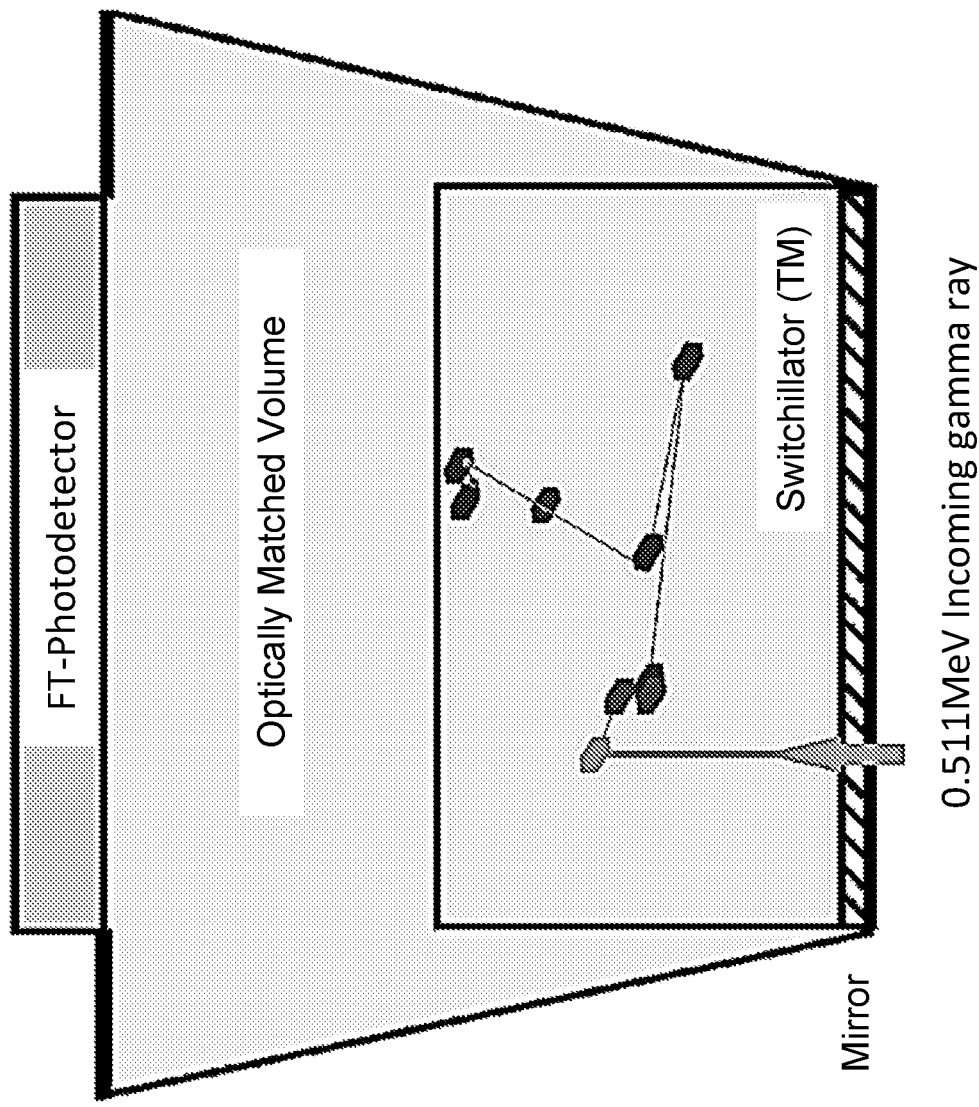
FIG. 4. A Geant4 simulation of a 511 KeV gamma-ray interacting in a hydrocarbon scintillating medium with H:C equal to 1.96 (specifically the scintillator used in the Kamland-Zen neutrino experiment), in an imaging module. (Gando, A., et al. "Search for *Majorana* neutrinos near the inverted mass hierarchy region with KamLAND-Zen." Physical review letters 117.8 (2016): 082503) The gamma-ray path is indicated with a gray line connecting the locations of Compton scatters. The energy deposition at each scatter is shaded, based on energy fraction.

This example is based on an analysis of a Geant4 simulation of a 511 KeV gamma-ray interacting in a hydrocarbon scintillating medium with H:C equal to 1.96, depicted in FIG. 4. The energy clusters associated with Compton scatters in the Geant4 simulation are shown. The gamma-ray path is indicated with a gray line connecting the locations of Compton scatters. The energy deposition at each scatter is color-coded from blue (low energy fraction) to red (high energy fraction). The gamma-ray loses energy at each Compton scatter until the gamma-ray energy is low enough for the photoelectric effect cross-section to dominate over the Compton process.

Imaging in Pixels

Image acquisition begins with the triggering of repeated fluor excitation and imaging cycles by the optical imaging system of an imaging module. After each excitation by the excitation light sources, the fluorescence detector system digitizes the fluorescence from the excited molecules in the Switchillator into a pixelated image.

The accurate reconstruction of the earliest gamma-ray interaction point in a Switchillator is facilitated by the pixelation, indexed in the 2D image plane by integers I and j. In the discussion of signal statistical significance below, $N_s(i, j)$ is the number of fluor molecules in pixel (i, j) activated by the deposited energy from a gamma-ray (i.e., signal); $N_b(i, j)$ is the number of fluor molecules activated by the excitation radiation (e.g., laser light) or other mechanisms other than energy deposition by the gamma-ray from an annihilation event (i.e., background).

The statistical significance of signal to background in a pixel is given by the ratio of the fluorescence intensity in the pixel to the mean intensity in neighboring pixels that are not involved in the gamma-ray interaction. The statistical significance of signal to background in the pixel, $R_s(i,j)$, in the limit where $N_b \ll N_s$, is given by:

$$R_s(i, j) \equiv \frac{N_s(i, j) + N_b(i, j)}{\sqrt{\langle N_b(i, j) \rangle}}, \quad (3)$$

where the average number of background molecules per pixel $N_b(i,j)$ can be found as an average of all of the scanned area, or from the illumination of an neighboring quiet area of the detector by the excitation light source.

Identifying Energy Clusters

As the Switchillator is scanned, the coordinates of the excitation light beam and the camera frame are recorded with the image. With this 3D information, Compton scattering events can be fully reconstructed, including their location, ionization energy deposition, and the trajectories of the scattered gamma-ray and recoil electron.

The gamma-ray interaction will produce a pattern in the fluorescence image corresponding to pixels containing activated fluor molecules that fluoresce with an intensity above background. The pixels can be assigned to energy clusters using image recognition, which can be performed by a variety of pattern recognition or image identification algorithms. An example algorithm implemented in a High Energy Physics 4π-geometry calorimetric detector is presented in Amidei et al., Nucl. Instr. and Meth. A269 (1988), p. 51 and Abe et al., Nucl. Instr. and Meth. A271 (1988), p. 387, and has been applied to Switchillator reconstruction, as described below.

The example algorithm starts by identifying 'seed' pixels having a high statistical significance (weight) by applying a pre-determined threshold ($T_s$). Pixels with $R_s(i,j)$ above $T_s$ are considered seed pixels. After all seed pixels are found, a lower, 'shoulder', threshold $T_{sh}$ is applied to all pixels. Clusters are formed by starting with each seed pixel in turn, adding neighboring pixels that are above $T_{sh}$ and similarly neighbors of neighbors, until completion. Typically, the eight nearest neighbor pixels of a seed pixel are adequate for cluster identification, although the range can be easily expanded. Small gaps can be bridged by applying cluster merging algorithms. The resulting energy cluster is assigned a location, energy, and statistical weight.

Figure 5:
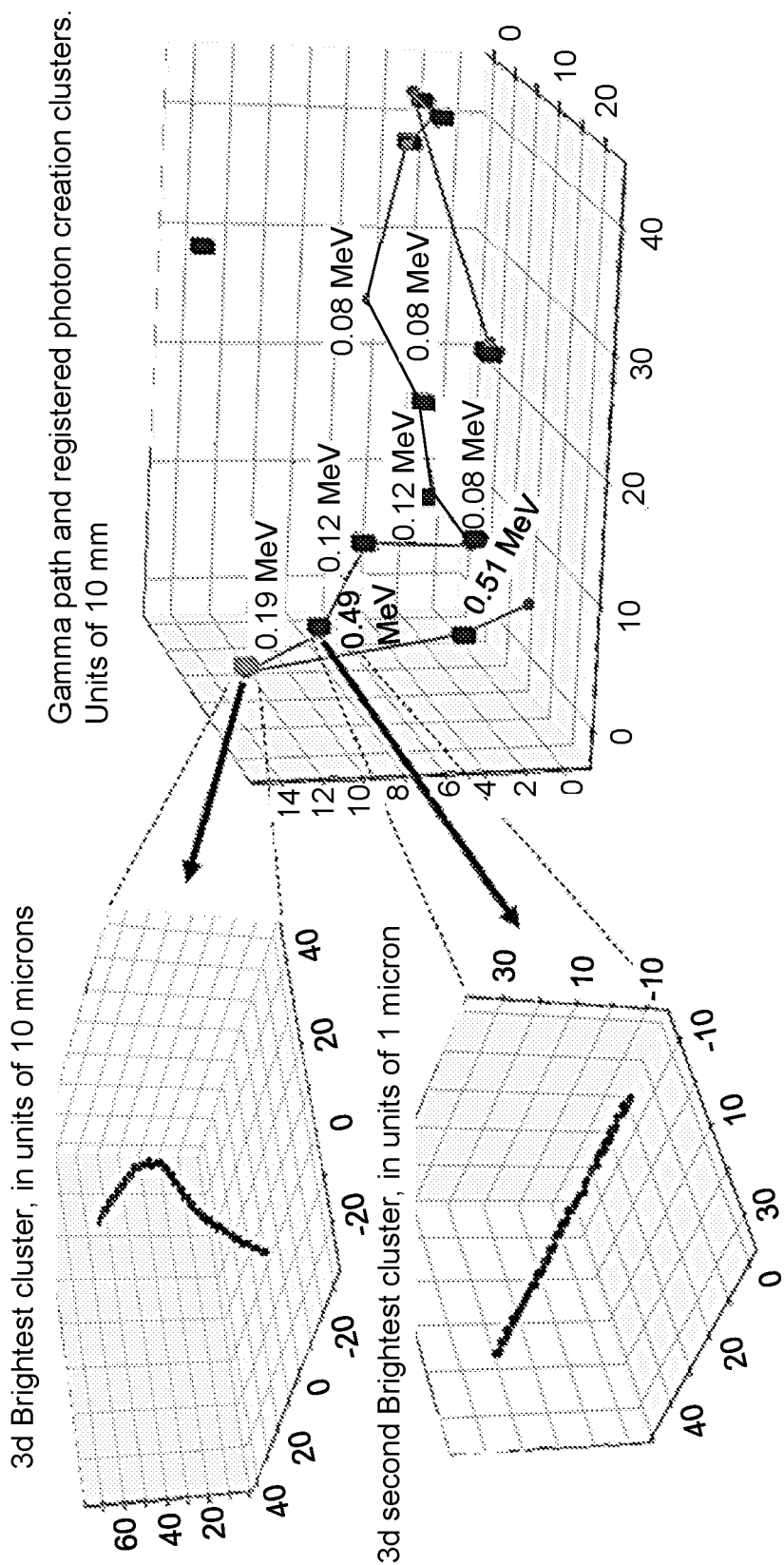
FIG. 5. Right: A view of a pixelated digital-camera image with 1 cm pixels showing energy depositions in the simulation of the 511 KeV gamma-ray of FIG. 4. Left: maps of energy depositions from two different Compton scattered electrons. Top-left: the energy deposition map showing the energy cluster corresponding to the most energetic Compton scatter, with a pixel resolution of 10 µm. Bottom-left: the energy deposition map showing the energy cluster corresponding to the second-most energetic Compton scatter, with a pixel resolution of 1 µm. The intensity of the energy deposition in each pixel is shaded, based on energy fraction.

The right-hand panel of FIG. 5 shows a pixelated image of the gamma-ray trajectory of FIG. 4 with a pixel size resolution of 10 mm. The top left panel is an enlarged image of the energy cluster corresponding to the most energetic Compton scatter from FIG. 4 using a pixel size of 10 μm, and the bottom left panel is an enlarged image of the energy cluster corresponding to the second second highest energy Compton scatter from FIG. 4. The density of energy deposition in each pixel is color-coded from blue (low energy fraction) to red (high energy fraction).

Figure 6:
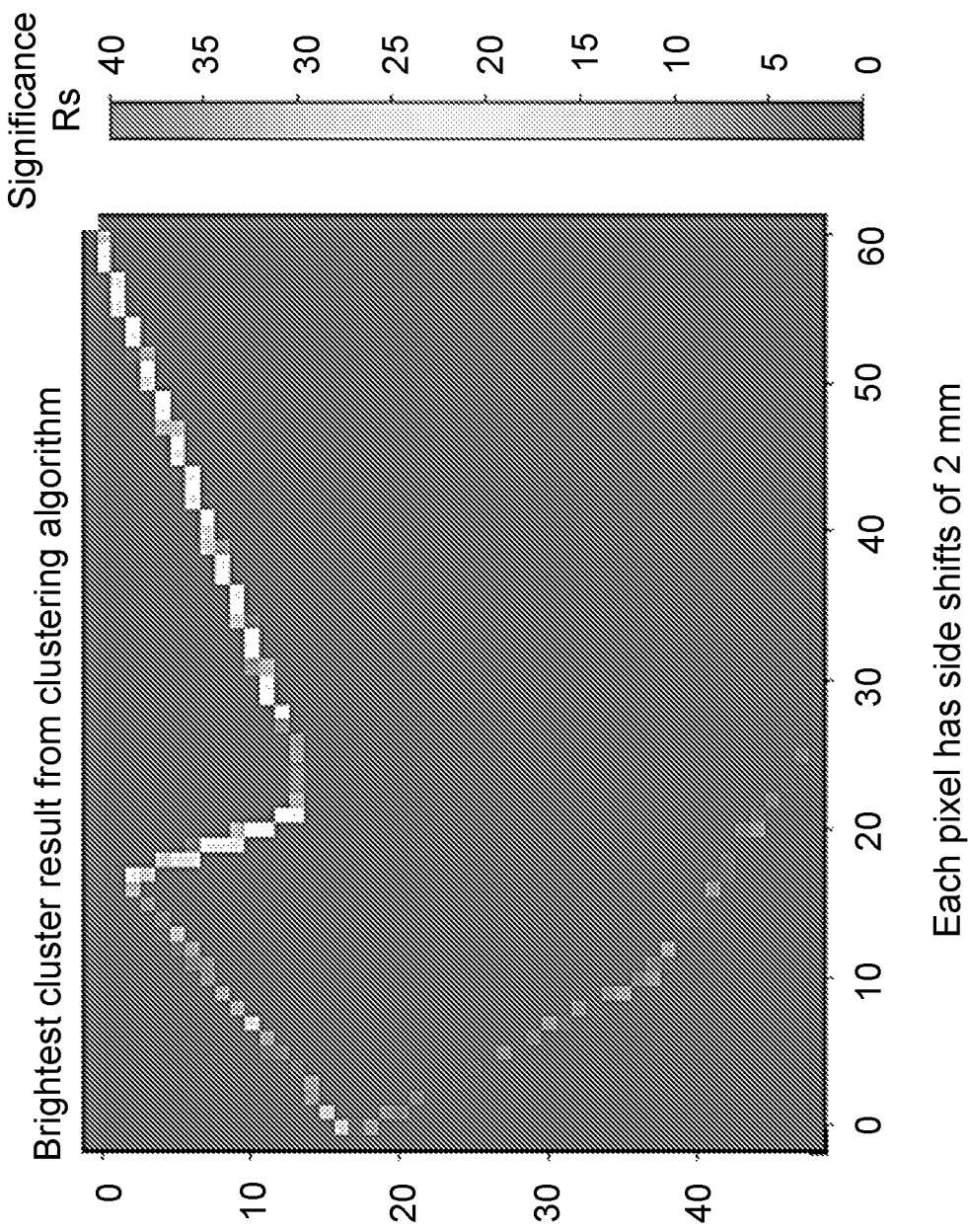
FIG. 6. The output of a seed-shoulder clustering algorithm applied to the energy cluster shown in the top left panel of FIG. 5, as described in Example 2.

After all energy clusters are found, the statistical significance (weight) for each cluster is given by the product of the statistical significance values of the pixels in the cluster. Thus, the statistical significance, $R_s$, for each cluster k can be given by:

$$R_s(k)=\Pi R_s(i,j),$$

where the multiplication ranges over the pixels in the cluster. A threshold on significance, for example 4σ, is then applied. FIG. 6 shows the result of this algorithm applied to the brightest energy cluster of FIG. 5.

Ordering Energy Clusters by Brightness

Figure 7:
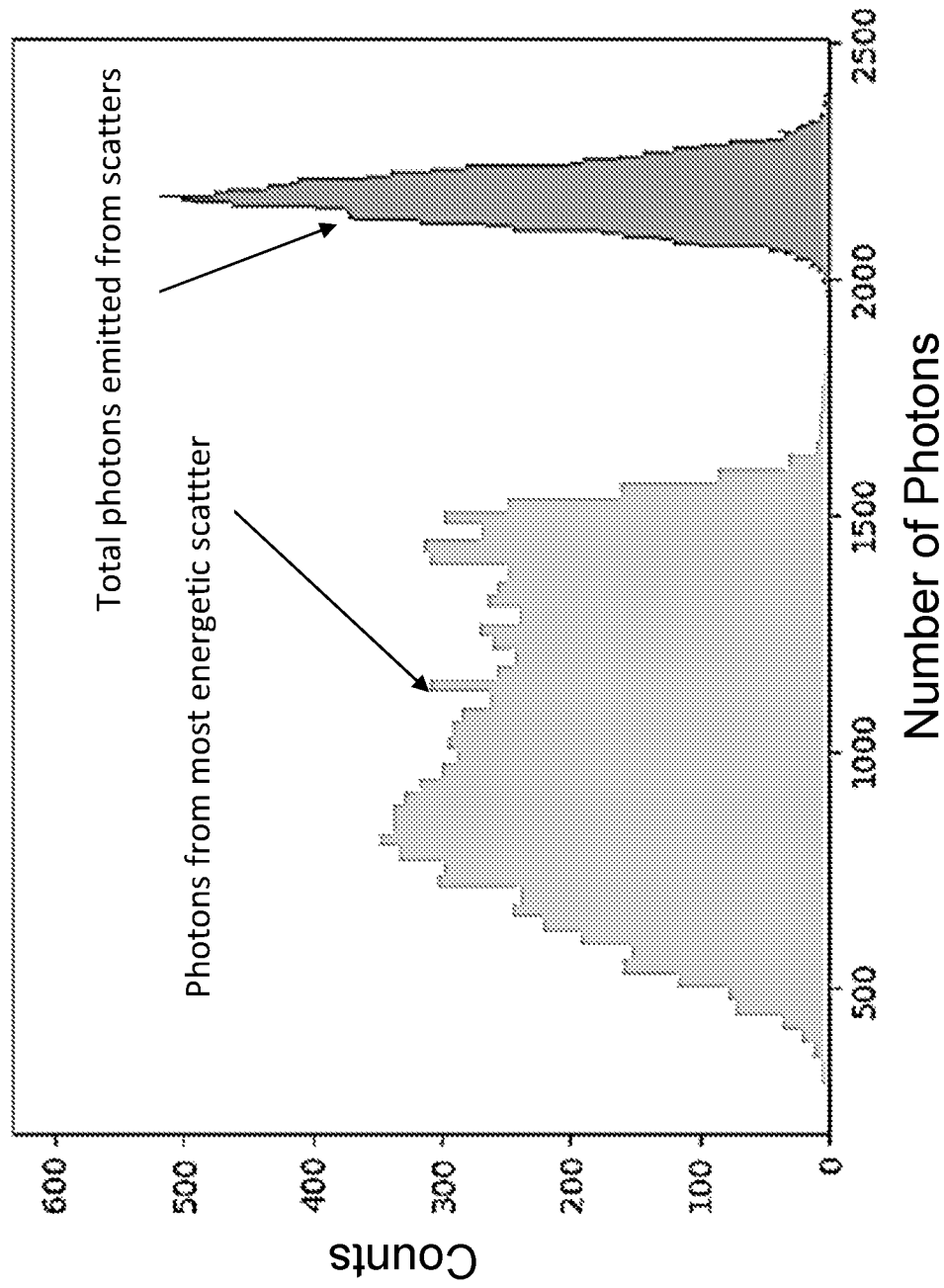
FIG. 7. The number of scintillation photons produced by the 511 keV gamma-ray in the Kamland-Zen-like scintillating medium, from a simulation of 10,000 gamma-rays. The number of photons from all Compton scatters is plotted on the right; the photons produced by the most energetic Compton scatter is plotted on the left.

As the number of activated fluors is proportional to the ionization energy, the 'brightness' of the pixels in a fluorescence image is related to the energy of the Compton electron. Earlier Compton scatters deplete more of the gamma-ray energy and will, in general, produce brighter pixel clusters with longer electron recoil tracks. This was confirmed by the Geant4 simulations of 511 KeV gamma-rays using the parameters of the liquid scintillator used in the Kamland-Zen detector, a hydrocarbon scintillating medium with H:C equal to 1.96. FIG. 7 shows the number of photons from all Compton scatters (right), and from the most energetic Compton scatter (left).

Figure 8:
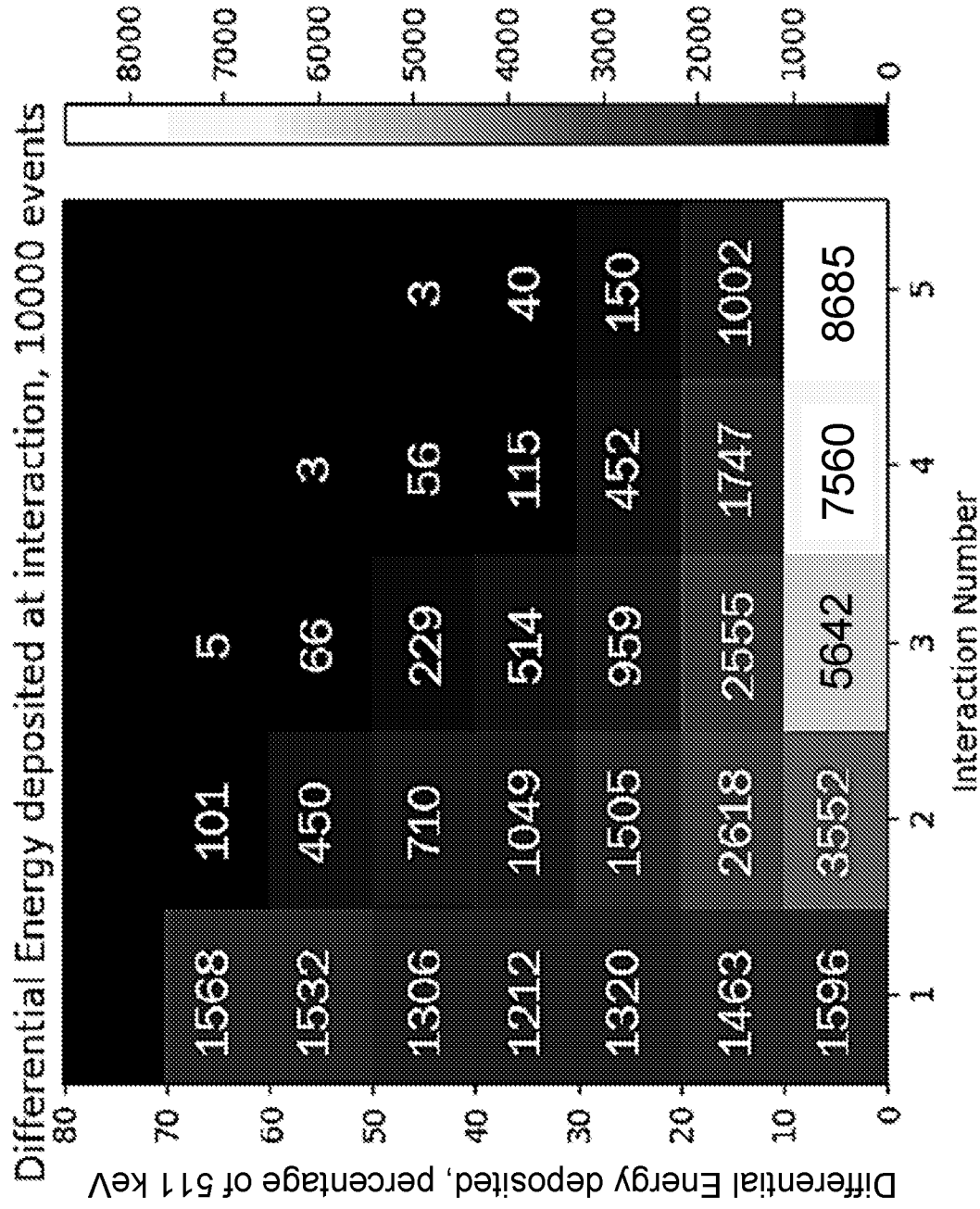
FIG. 8. Tabulation of the fractional energy deposited by the 511 keV gamma-ray in successive Compton scatters in the Kamland-Zen scintillating medium. The rows correspond to the fraction of 511 keV deposited in each interaction. The columns represent the first through fifth interactions between the gamma-ray and the scintillating medium. The entries are event counts from 10,000 simulated gamma-rays.

FIG. 8 shows a tabulation of the fractional energy in the first five successive Compton scatters. The rows correspond to the fraction of 511 keV deposited in each interaction. The columns represent the interaction number of the gamma-ray, with 1 being the first Compton scatter, tabulated up to the first five scatters. The entries in the table are event counts out of 10,000 simulated gamma-rays. The brightest event cluster is produced by the earliest Compton scatter approximately 55% of the time, the second Compton scatter 25% of the time, and the third Compton scatter 11% of the time.

Constructing a Line-of-Response

Figure 9:
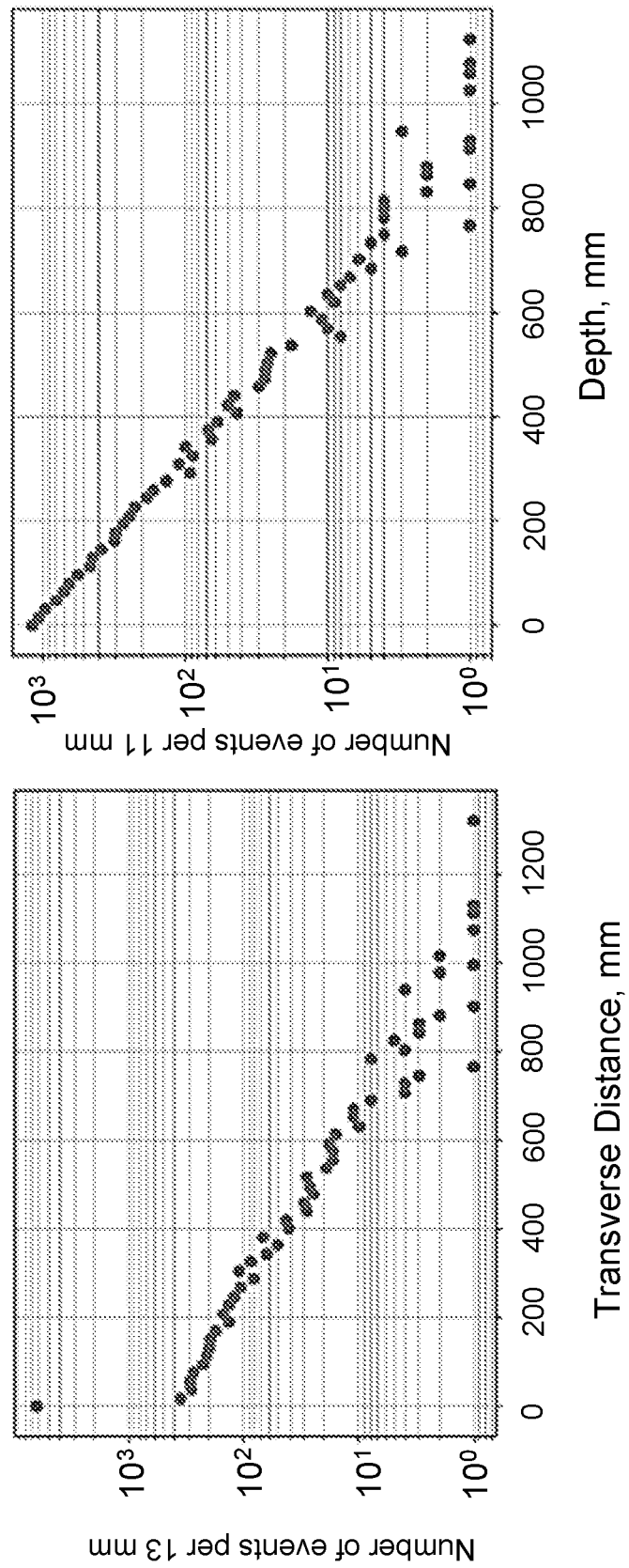
FIG. 9. The longitudinal [Left] and transverse [Right] positions of the brightest interaction between the 511 keV gamma-ray and the scintillating medium in a line-of-response reference frame in the Kamland-Zen hydrocarbon scintillating medium. Ninety percent of the gamma-rays interact within 30 cm of the entrance to the active Switchillator volume.
Figure 11:
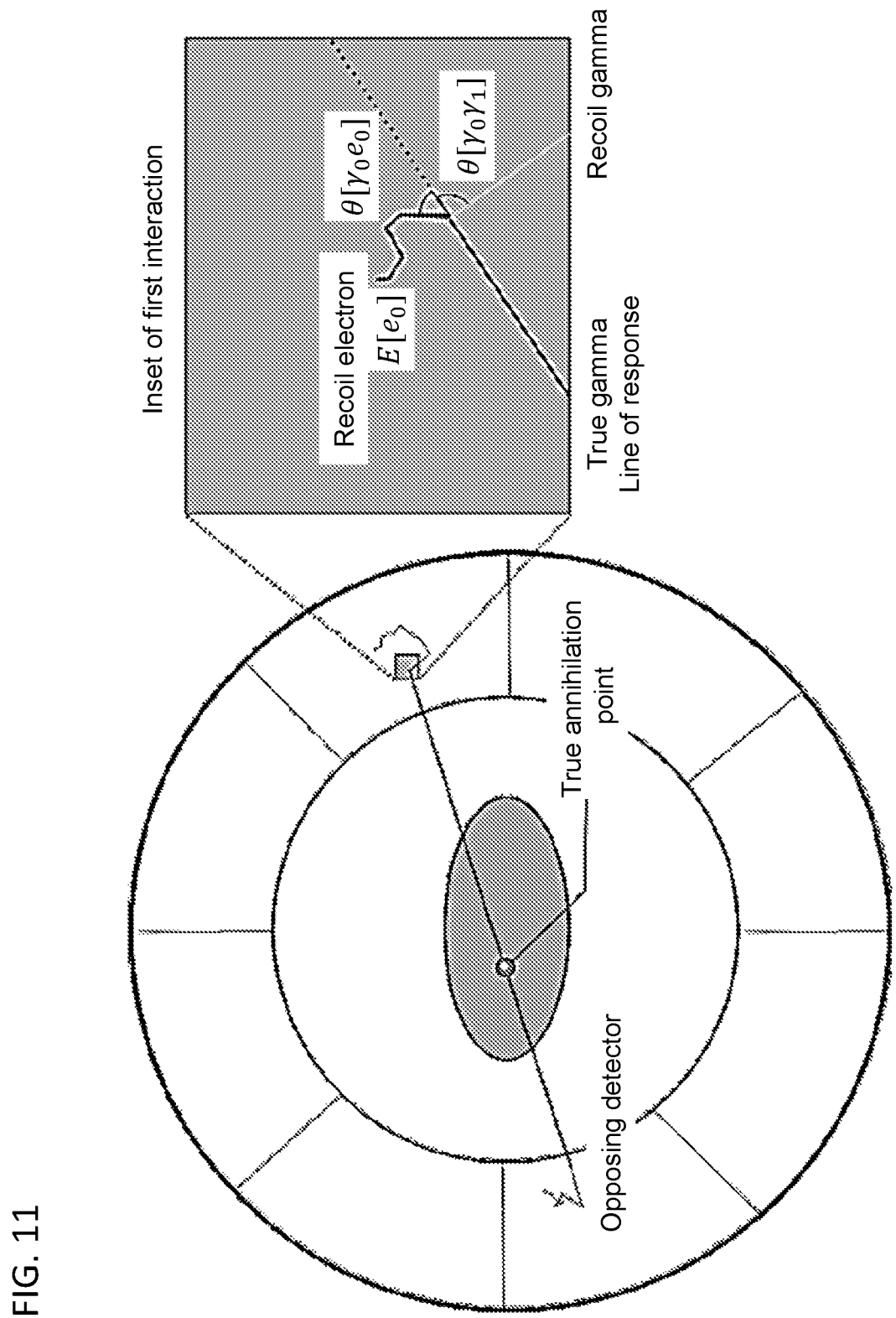
FIG. 11. An example LOR drawn between the first Compton scatter in each of two opposing imaging modules, in the case of no gamma-ray scattering in the patient.

The LOR is the line drawn between the initial gamma-ray interaction points in the Switchillators of two imaging modules. FIG. 11 shows an example LOR drawn between the first Compton scattering event in each of two opposing imaging modules, in the case of no scattering in the patient. A LOR reference system is defined here as the orthogonal directions along (longitudinal) and transverse to the LOR. The optical imaging system provides improved spatial resolution of the LOR for a positron-electron annihilation event by identifying, on a statistical basis, the location of the earliest energy-deposition event for each gamma-ray of a coincident pair. FIG. 9 shows the longitudinal [Left] and transverse [Right] positions of the brightest interaction between the 511 keV gamma-ray and the scintillating medium in the line-of-response reference frame in the Kamland-Zen hydrocarbon scintillating medium.

The pixelated images of the energy clusters provide information on the direction of the Compton recoil electron after a Compton scattering event, which can be used to identify the end points of a LOR. Because the scattering angle of a Compton scattered gamma-ray and its recoil electron are completely constrained by 2-body Compton kinematics (Compton, *Phys. Rev.* 21 (5) (1923), pp. 483-502), the geometric pattern of energy clusters in the pixelated optical image enables a fit to the locations, brightness (energy deposition), and/recoil directions from which the path and entry point of a gamma-ray in the scintillating medium can be reconstructed. Moreover, once the energy cluster corresponding to the first gamma interaction has been identified, the starting end of the Compton-scattered electron track, which corresponds to the first gamma-ray/electron collision point can be determined, on a statistical basis, based on energy loss and scattering along the imaged electron track, and by the Compton 2-body kinematic constraints on the energies and spatial relationships among clusters.

Figure 10:
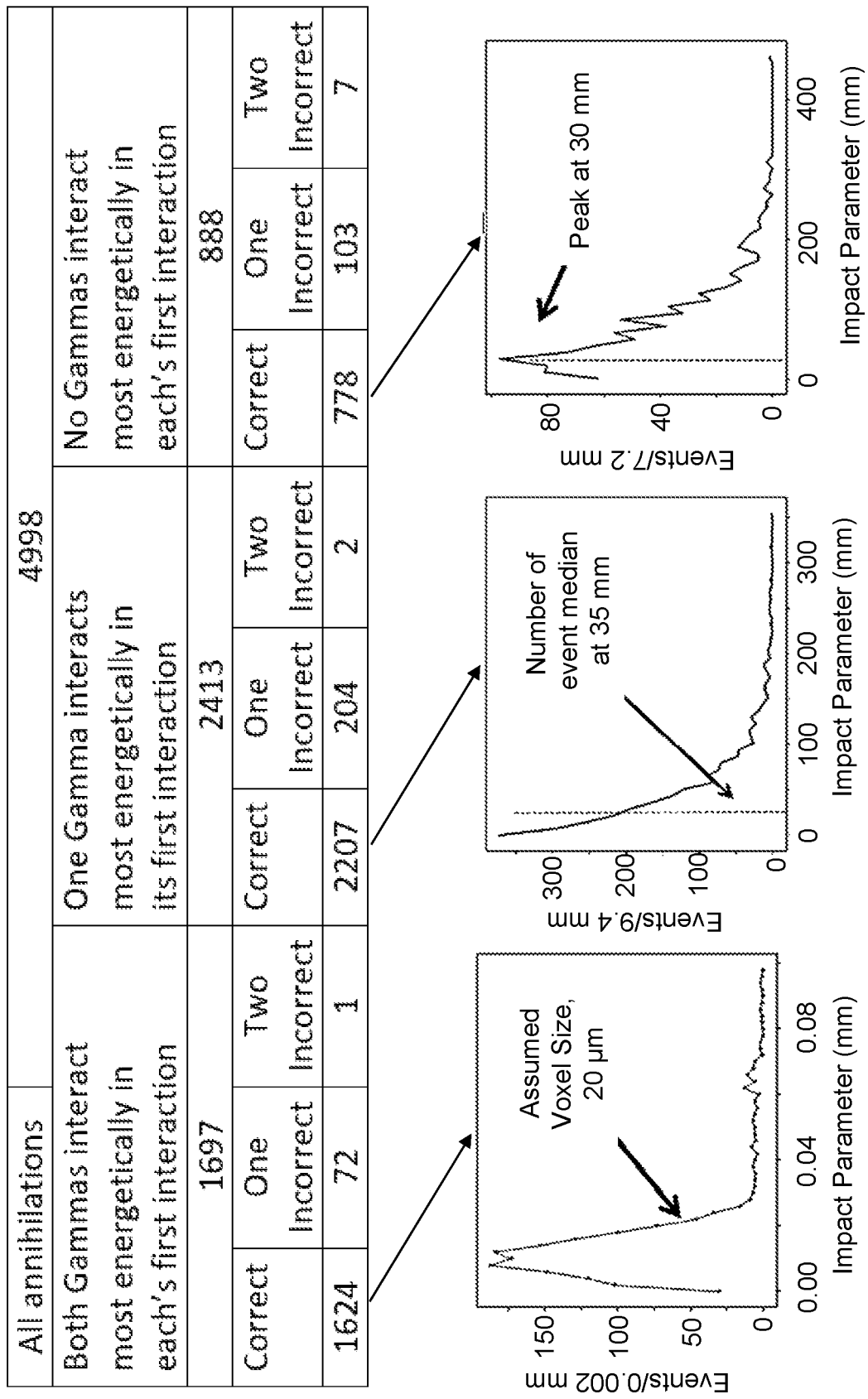
FIG. 10. Top: A tabulation of the number of positron-electron annihilation events, out of 10,000 simulated, in which the first interaction of the gamma-ray is the most energetic Compton scatter for both gamma-rays of a coincident pair, the first scatter for one of the two gamma-rays is the most energetic Compton scatter, and the first scatter for neither of the two gamma-rays is the most energetic Compton scatter. These three columns are further subdivided into the cases in which the direction of the recoil electron is correctly reconstructed for both, one, and neither gamma-ray. Bottom: The corresponding plots of the impact parameter (distance of closest approach) of the LOR to the true emission point in the sample. When both first interactions are the most energetic Compton scatter, the impact parameter is predominantly less than 30 µm for a voxel size of 20 µm. If either first interaction is not the most energetic, the median impact parameter is 35 millimeters (35,000 microns), and consequently these events have little impact on resolution and contrast, forming a featureless flat background to true signal.

FIG. 10 shows a table of annihilation event counts partitioned by whether the first energy deposition for one, both, or neither gamma-ray for a coincident gamma-ray pair was the most energetic Compton scatter in the module, and further partitioned by whether the starting point of the recoil electron track for one, both, or neither of the gamma-rays was correctly reconstructed. For the Compton scatters where the starting end of the electron track was correctly identified, the impact parameter of the LOR for the coincident gamma-ray pair compared to the true annihilation point is plotted. In the case where both of the first interactions are the most energetic Compton scatters, the impact parameter is almost always less than 30 μm, when the voxel size is 20 μm. For events in which both gamma-ray interactions are correctly reconstructed, the resolution on the LOR is characterized by the voxel size, typically 10-30 μm. If either first interaction is not the most energetic Compton scatter, the median impact parameter is 35 millimeters and the contrast is low.

The precision of the LOR can be further improved based on iterative imaging of the fluors, with the possibility of hundreds to many thousands of excitations for the same activated fluor pattern. The example optical system of FIGS. 2 and 3 is designed to enable advanced imaging that supports a number of techniques, including successively increasing magnification, optical steering of the exciting light and the camera imaging paths, multiple wave-length excitations, time-dependence of the fluorescence allowing for the use of multiple fluors, and optimization of specific sub-measurements.

The ability to perform iterative imaging is ideal for real-time adaptive imaging, in which the imaging algorithm parameters are optimized on the accumulated image at each time, and on machine learning. The parameters include kinematic information from each scattering event, relative ordering and brightness of the scatters and prior information from the accumulating sample image.

Figure 12:
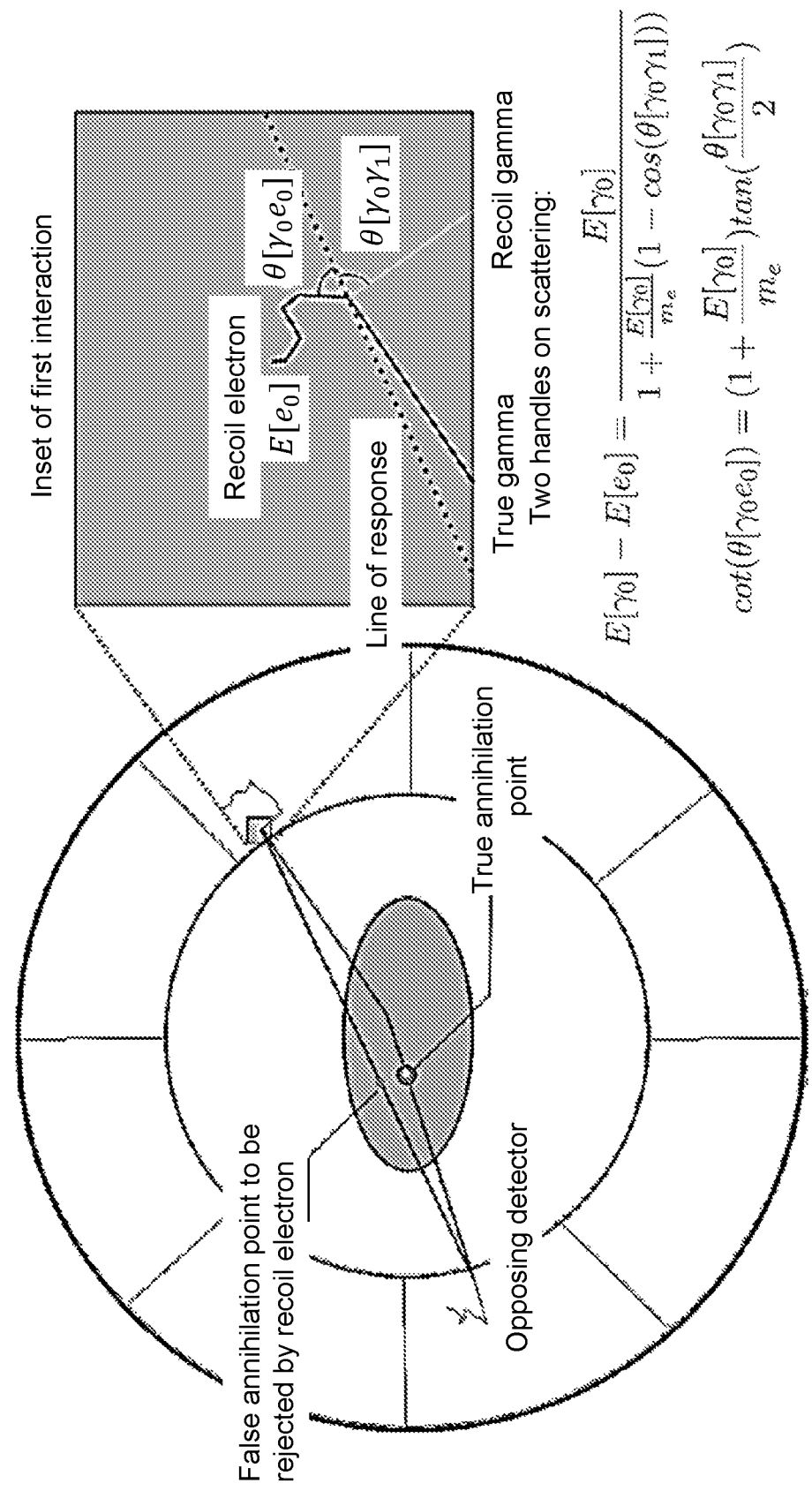
FIG. 12. An example LOR drawn between the first Compton scatter in each of the opposing imaging modules, in the case of in-patient gamma-ray scattering. The Compton scatter is fully-constrained by the Compton 2-body kinematical equations.
Figure 13:
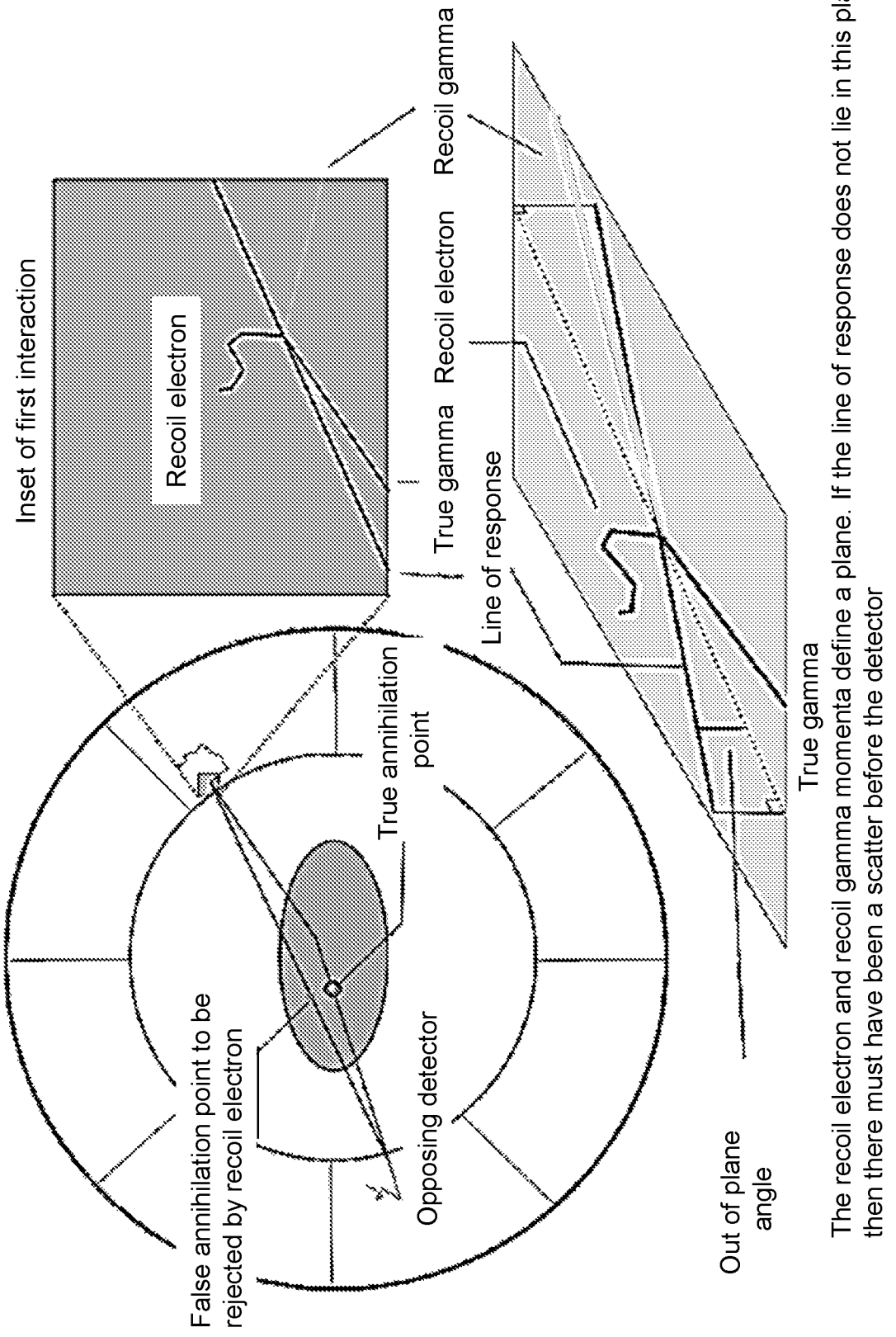
FIG. 13. An example LOR drawn between the first Compton scatter in each of the opposing imaging modules, in the case that gamma-ray scattering in the patient is out of the plane reconstructed in the imaging module of the Compton scattered gamma and the recoil electron.

FIGS. 12 and 13 illustrate how the optical imaging system can used to further improve the reconstruction of a gamma-ray source by identifying and eliminating false coincidences. FIG. 12 shows an example LOR drawn between the first Compton scatter in each of two opposing imaging modules in the case where one gamma-ray has undergone in-patient scattering. LORs that are mis-measured due to gamma-ray in-patient scattering will typically be distributed over an area large compared to the feature resolution, and can be background-subtracted.

The two-body kinematics of Compton scattering allows an additional rejection of annihilation events with in-patient scattering. As shown in FIG. 13, the recoil electron and the Compton scattered gamma-ray momenta define a plane in which the LOR for a coincident gamma-ray pair must lie. The statistical significance of the deviation from this plane can be used as a factor in the event weight during gamma-ray source image reconstruction.

Spatial Resolution along a Line-of-Response

The Switchillator-based PET systems accommodate advanced Time-of-Flight (TOF) techniques for identifying an annihilation event with high spatial resolution along a LOR. In addition, the connection between the Switchillator and TOF systems goes both directions: the TOF system provides seeds locations for the Switchillator spatial cluster finding, and then, after full analysis of the gamma-ray trajectories in the modules, the Switchillator system uses the precise spatial information to sharpen the TOF results. Sharpening the probability distribution of the vertex position along the LOR both provides a more significant image and diminishes background events from fluor molecules excited by sources other than the scattered electron.

The spatial resolution along the LOR is determined by the location of the interactions of each gamma-ray in its respective module, the response time and yield of the scintillating medium, the details of collecting the scintillation light in the module, and the relative timing of the arrival of the two gamma-rays. A simulation of 1000 gamma-ray interactions in the Kamland-Zen scintillator finds >2000 scintillation photons are produced in the wavelength range 360-785 nm.

Figure 14:
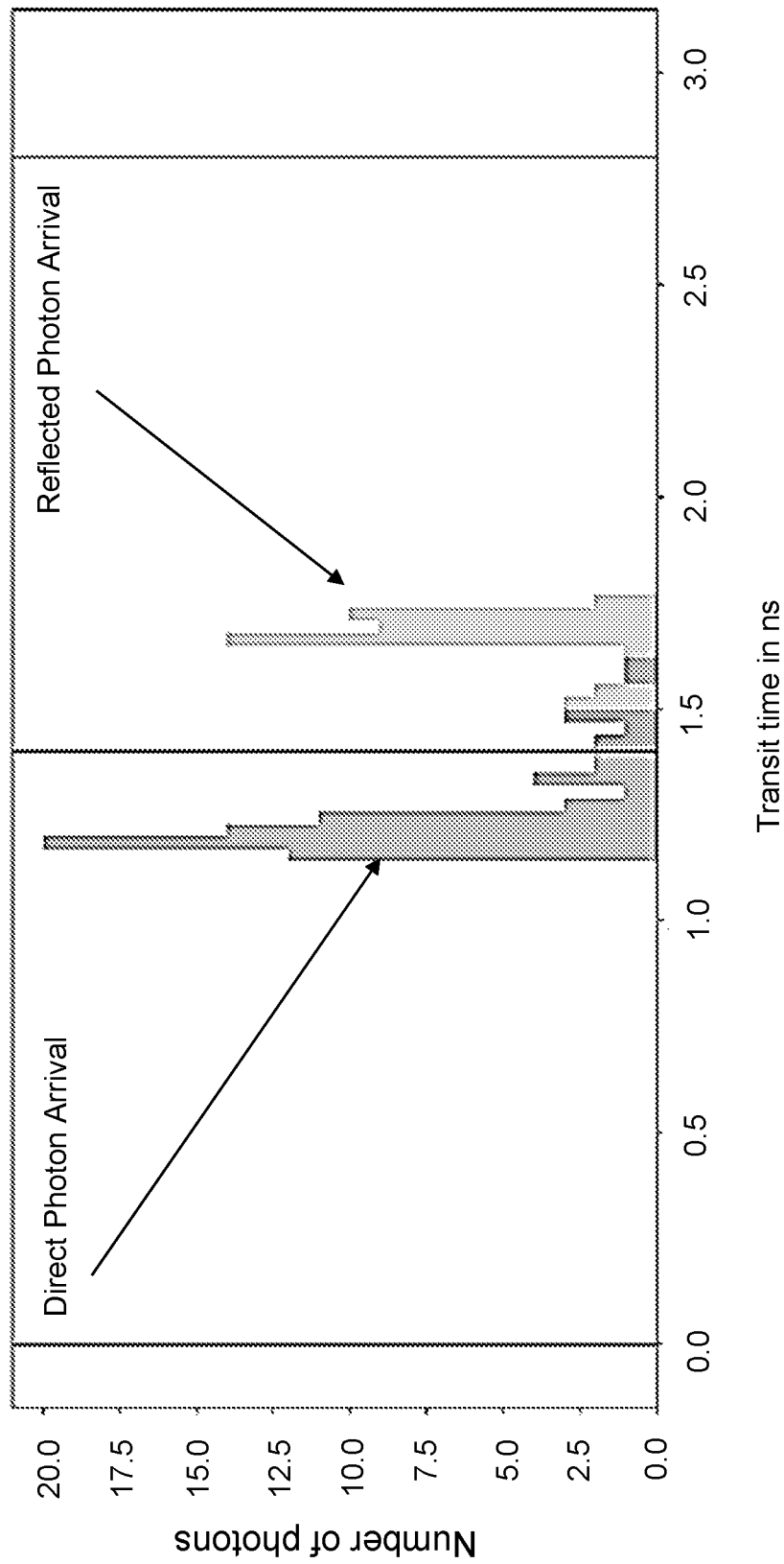
FIG. 14. For one simulated event, the distribution in the time between the arrival of the 511 keV gamma-ray at the front face of an imaging module (t=0) and the arrival of individual scintillation photons at an FT-photodetector on the back surface in the ideal case of a fast scintillator with zero lifetime. Distributions are shown for both the direct and reflected light. This event occurs near the back of the imaging module so that the photon times are near the light-time to cross the module, assumed here to be 300 mm. The gamma-ray travels at the speed of light, c; the photon velocity is lower by a factor of the index of refraction, here taken to be 1.4.
Figure 15:
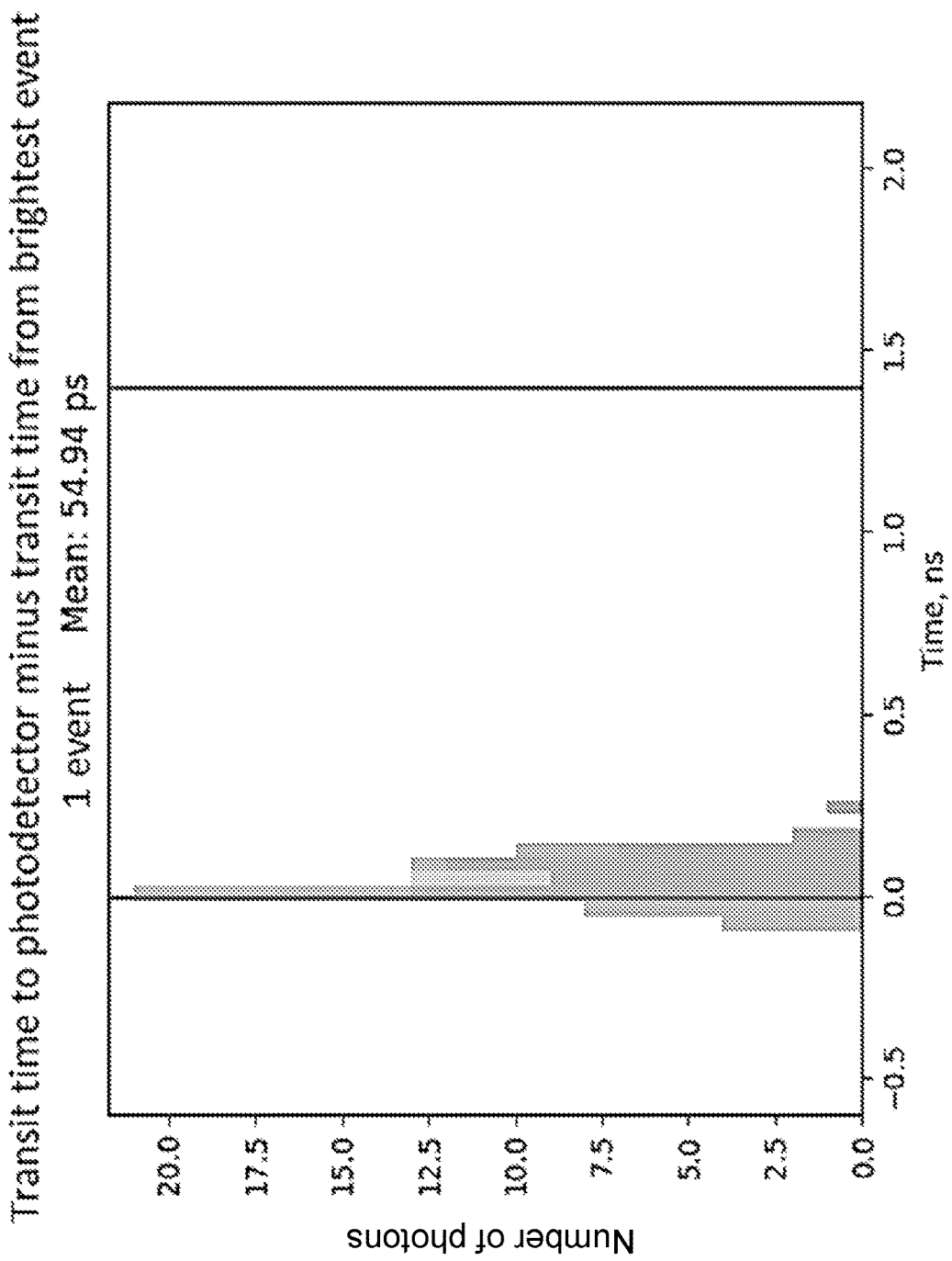
FIG. 15. For the same selection criteria as in FIG. 14, the distribution in the time of emission of the photons from the brightest cluster.

FIG. 14 shows the transit time between the gamma-ray entry at the front face (t=0) and the first photon to arrive at the FT-photodetector for direct and reflected photons in the example implementation of FIGS. 2 and 3. FIG. 15 shows the distribution of FIG. 14 corrected for the photon transit time, assuming the photons were emitted from the brightest cluster.

Figure 16:
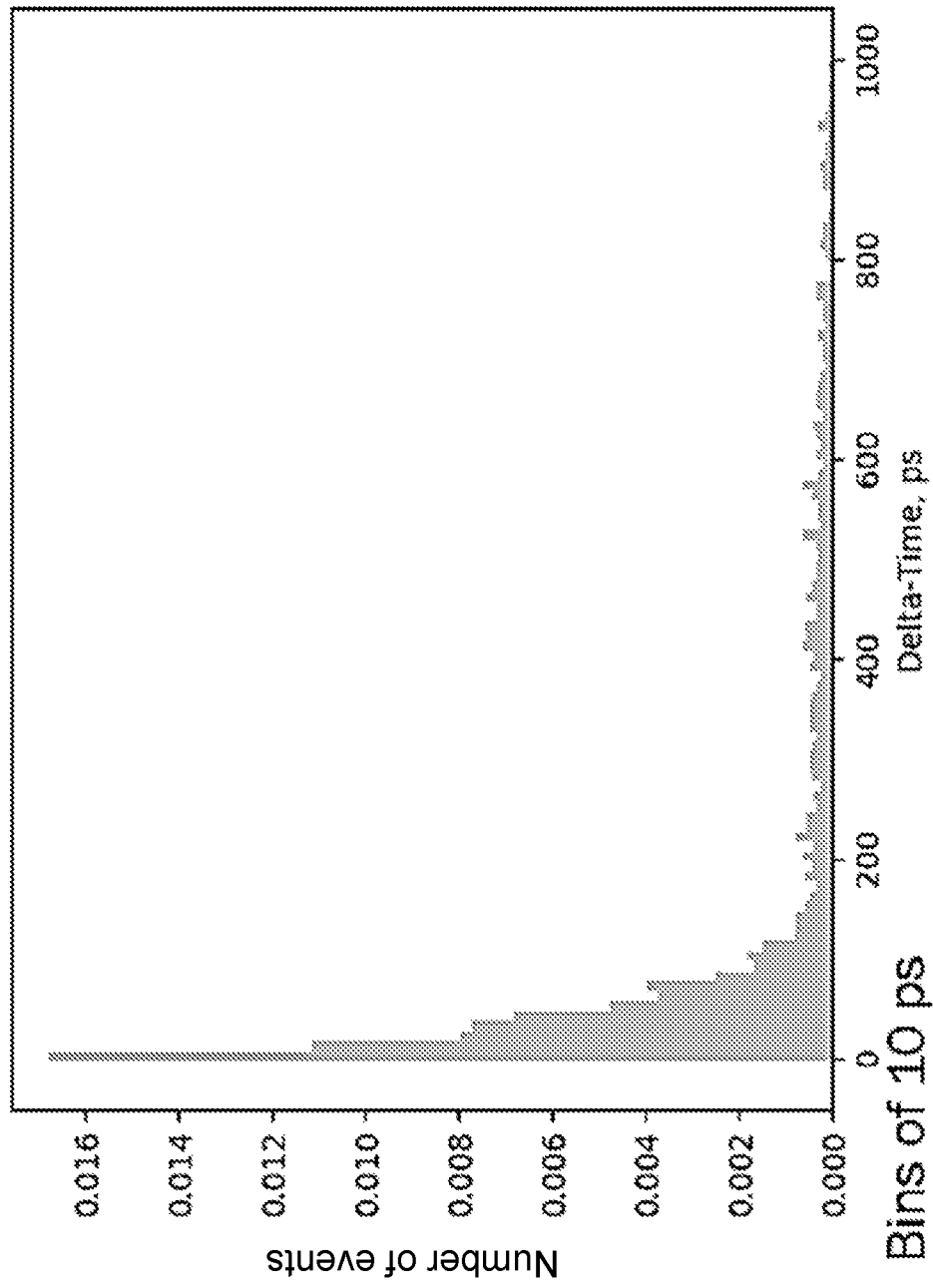
FIG. 16. Time-of-flight resolution for an on-axis point-source sample, derived from the arrival time of the first photon identified for each of the two brightest clusters. The scintillator is assumed to have the limited Kamland-Zen light yield, but had been chosen for a short lifetime, such that the emission time of the first photon arriving is negligible.

FIG. 16 shows the intrinsic TOF resolution distribution for annihilations in the sample from a Geant4 simulation with an infinitely fast scintillator. The TOF resolution may be determined y by the speed and yield of the scintillator fluor (Drew R. Onken et al. *Mater. Adv.* 1 (1 2020), pp. 71-76. doi: 10.1039/D0MA00055H.), as the LAPPD detector in the example implementation has single photon resolution less than 50 psec.

In addition to scintillation light, there is a small production of Cherenkov light, weighted toward the early Compton scatters for which the gamma-ray has a higher energy and so a higher probability of producing an electron with velocity over Cherenkov threshold. Selecting the earliest photon enhances these photons. In addition, the LAPPD records the position of detected Cherenkov photons for comparison with prediction.

Low-Dose High-Resolution PET Imaging

The high spatial resolution for individual positron-electron annihilations allows the formation of useful PET images with significantly lower radiation dose to a patient than in current practice.

Figure 17:
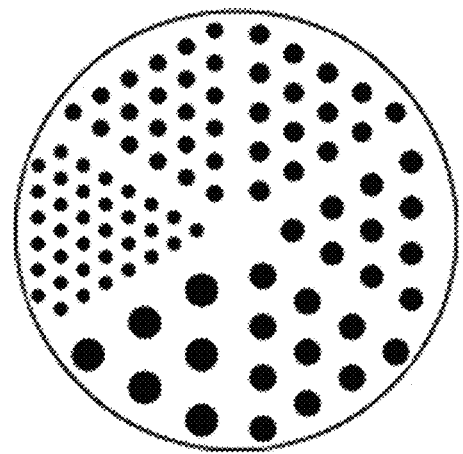
FIG. 17. The specifications (center) and figures (left and right) of the commercially available Standard Jaszczak Phantom used to test and calibrate PET and SPECT scanners. The phantom contains cylinders filled with a radioactive tracer solution in a tight-fitting volume filled with lower tracer concentration. The spheres in the photograph were not simulated.
Figure 17:
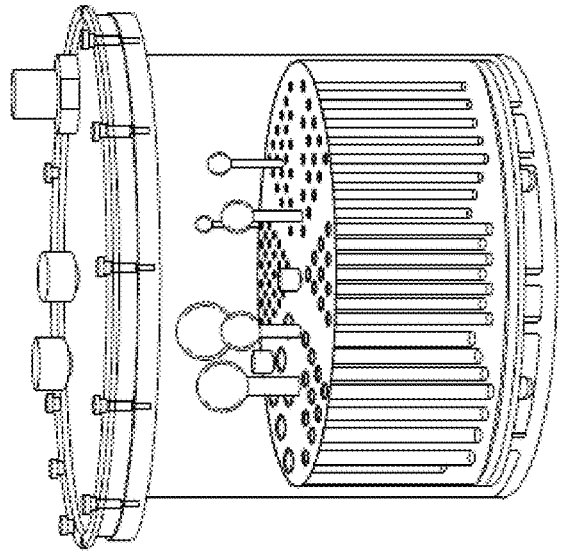

FIG. 17 presents the specifications (center) and figures (left and right) of the commercially available Standard Jaszczak Phantom™ (Biodex Medical Systems, Inc, "*Nuclear Medicine and molecular imaging, devices and supplies*"; Catalog 125, pg. 84, Model No. 043-762, 2020) used to test and calibrate PET and SPECT scanners. The phantom contains cylinders filled with a radioactive tracer solution ('hot rods'), in a tight-fitting volume filled with a solution containing a lower tracer concentration (background).

Figure 18:
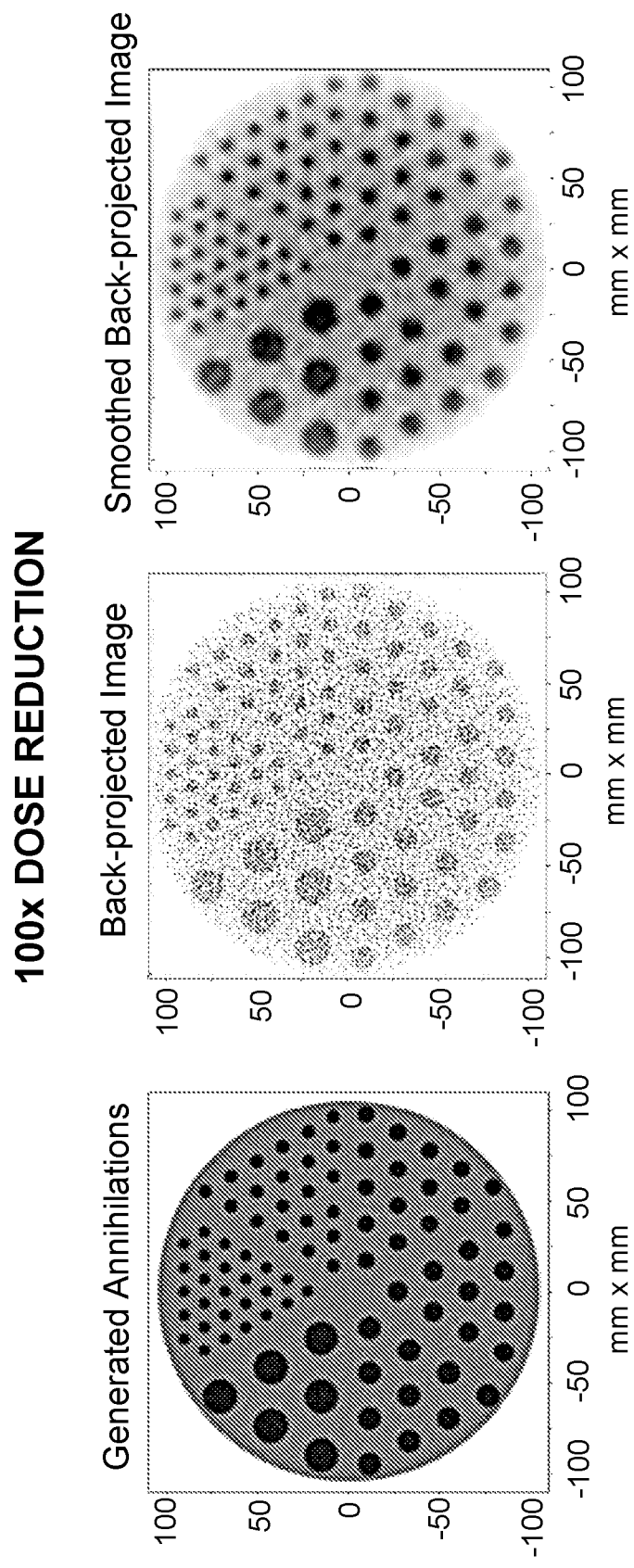
FIG. 18. Left: Generated annihilation coordinates from a simulation of the Standard Jaszczack Phantom™ described in FIG. 17, but with two cylinders of 10 cm length and the same diameter, each containing a 'background' loading of 100 Bq/ml of $^{18}$F appended to the top and bottom faces of the standard phantom. Center: The filtered backprojection of the left panel, with a pixel size of 1 mm. Right: The center panel image smoothed by a Gaussian filter of 2 mm. The hot rods are loaded with 300 Bq/ml of $^{18}$F, while the background is loaded with 100 Bq/ml of $^{18}$F. The efficiency of reconstructing the LOR to within a sigma of 20 µm is assumed to be 10%; the detector is assumed to have a radius of 30 cm and an axial length of 30 cm, corresponding to the length of a single module; the exposure is set to 10 minutes.

The left-hand panel of FIG. 18 shows the simulated annihilation coordinates for the Jaszczak phantom described in FIG. 17. The center panel displays the filtered back-projection (Dudgeon and Mersereau, "*Multidimensional digital signal processing*". Prentice-Hall, 1984) of the left panel, with a pixel size of 1 mm. The right-hand panel displays the center panel smoothed by a gaussian filter of 2 mm. The hot rods are loaded with 300 Bq/ml of $^{18}$F, while the background is loaded with 100 Bq/ml of $^{18}$F, concentrations that are a factor of 100 lower than typical practice in human patients. The efficiency of reconstructing the LOR to within a sigma of 20 μm is assumed to be 10%; the scanner is assumed to have a radius of 30 cm and an axial length of 18 cm; and the exposure time is 10 minutes. It should be noted that the line-integral of background in this simulated geometry is smaller than would be encountered in a patient.

Figure 19:
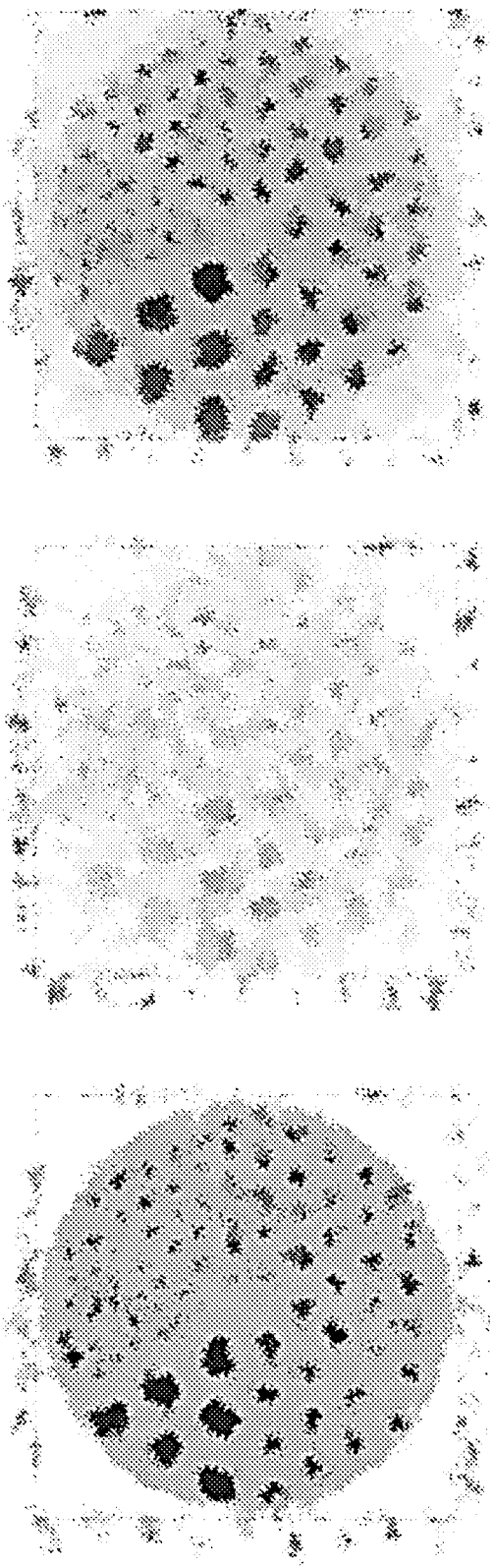
FIG. 19 shows the simulated annihilation coordinates for the Jaszczak phantom described in FIG. 18, but with two additional cylinders of 10 mm length and the same diameter, but without hot rods, added to each end in order to simulate additional background from a longer line-integral.

The left-hand panel of FIG. 19 shows the simulated annihilation coordinates for the Jaszczak phantom described in FIG. 18, but with two additional cylinders of 10 mm length and the same diameter, but without hot rods, added to each end in order to simulate additional background from a longer line-integral. The center-panel displays the filtered back-projection of the left-hand panel, with a pixel size of 1 mm. The right-hand panel shows the center panel smoothed by a gaussian filter of 2 mm. As in the case of FIG. 18, the hot rods are loaded with 300 Bq/ml of $^{18}$F, while the background is loaded with 100 Bq/ml of $^{18}$F, concentrations that are a factor of 100 lower than typical practice in human patients. The efficiency of reconstructing the LOR to within a sigma of 20 μm is assumed to be 10%; the scanner is assumed to have a radius of 30 cm and an axial length of 18 cm; and the exposure time is 10 minutes.

Example 3. RISC-Based Gamma-Ray Detection

This example provides illustrative guidance for methods of RISC-based scattering event identification and sequencing.

This example is a simulation of a Compton-scattered electron in a liquid scintillator close to a planar, finely-pixelated photodetector, such as an array of MCP-PMTs or SiPMs, with time resolutions in the tens of picoseconds. As shown in FIG. 20 panels (a)-(d), the expanding spherical wavefront of scintillation photons generated by the Compton scattering event impinges on the photodetector image plane (front face), producing an expanding circular (FIG. 20, panel (a)) pattern, and then ring-shaped (FIG. 20, panels (b)-(d)) patterns. The use of a scintillating medium that generates sufficient scintillation light and has short rise and fall-times enables images of the scintillation photons to be recorded at a series of time intervals. The time and location of the Compton scatter can be reconstructed from the photon transit times and path to within a few cm (for example, within 2 to 10 cm). This is less than the average distance between Compton scattering events of a gamma-ray within the scintillating medium, so the measurements of the individual photon times and positions can contribute not only to the identification of the time and location of the earliest Compton scatter, but also to the time-ordering of the successive Compton scatters.

The photodetector simulated for this example was a large-area MCP-PMT, such as the 20-cm square LAPPD™, equipped with patterned pad anodes with sub-mm spatial resolution and single photon time resolutions less than 50 psec at a channel count per unit area of less than 2000 channels/m². High-speed inexpensive low-power waveform sampling circuitry allowed for time slicing at 10-15 GS/sec. Details of the LAPPD, the patterned anodes, and the waveform sampling circuitry can be found in the following references: E. Oberla and H. J. Frisch; Charged particle tracking in a water Cherenkov optical time projection chamber, Nucl. Inst. Meth. Phys. Res. A. Volume 814, 1 Apr. 2016; B. W. Adams, A. Elagin, H. Frisch, R. Obaid, E. Oberla, A. Vostrikov, R. Wagner, J. Wang, M. Wetstein; Timing Characteristics of Large Area Picosecond Photodetectors; Nucl. Inst. Meth. Phys. Res. A., Vol. 795, pp 1-11 (Sept. 2015); E. Angelico, T. Seiss, B. W, Adams, A. Elagin, H. J. Frisch, E. Spieglan; Capacitively coupled pickup in MCP-based photo-detectors using a conductive, metallic anode Nucl. Inst. Meth. Phys. Res. A. (Oct. 2016); Jinseo Park, Fangjian Wu, Evan Angelico, Henry J. Frisch, Eric Spieglan; Patterned anodes with sub-millimeter spatial resolution for large-area MCP-based photodetector systems Nuclear Inst. and Methods in Physics Research, A 985 (2021) 164702; 22 Sept, 2020; E. Oberla, in proceedings of the Workshop on Picosecond Photon Sensors, Clermont-Ferrand, 2014; E. Oberla, J.-F. Genat, H. Grabas, H. Frisch, K. Nishimura, and G. Varner; A 15 GSa/s, 1.5 GHz Bandwidth Waveform Digitizing ASIC, Nucl. Instr. Meth. A735, 21 Jan., 2014, 452; and E. Oberla, J. Porter, and J. Stahoviak; PSEC4A: A 10 GSa/s Waveform Sampling ASIC with Multi-Event Buffering Capability; Proceedings of TWEPP 2018; Antwerp, Belgium (Sept. 2018).

The initiating gamma-ray travels at c, the speed of light in vacuum; the optical photons, however, travel at $c/n(\lambda)$, where $n(\lambda)$ is the (wavelength-dependent) index of refraction of the scintillating medium. The wave-front consequently expands at approximately $300/n(\lambda)$ microns per psec. By way of illustration, for toluene at a wavelength of 500 nm, $n(\lambda)$ is approximately 1.5, leading to a wave-front velocity of 1 cm/50 psec. The image consequently will be dominated by the number of photons at the leading edge of the wave.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" can be only one or can mean "one or more." Both embodiments are covered.

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A positron emission tomography system comprising a plurality of imaging modules, the imaging modules comprising:
   a scintillator compartment containing a low atomic number scintillating medium comprising one or more fluors, the scintillator compartment having a front face and a back face;
   a photodetector system comprising:
      one or more photodetectors optically coupled to the scintillator compartment and configured to detect scintillation photons generated in the scintillating medium; and
      one or more reflecting surfaces configured to reflect scintillation photons generated in the scintillating medium to the one or more photodetectors;
   an optical imaging system comprising:
      one or more excitation light sources optically coupled to the scintillator compartment and configured to direct excitation light onto the scintillating medium; and
      one or more fluorescence detectors optically coupled to the scintillator compartment and configured to detect fluorescence generated by the fluors in the scintillating medium.

2. The positron emission tomography system of claim 1, wherein the scintillating medium is a liquid.

3. The positron emission tomography system of claim 1, wherein the scintillating medium is a solid.

4. The positron emission tomography system of claim 1, wherein the scintillating medium is a gel.

5. A method for imaging a sample using a positron emission tomography system comprising:
   a plurality of imaging modules, the imaging modules comprising:
   a scintillator compartment containing a low atomic number scintillating medium comprising one or more fluors, the scintillator compartment having a front face and a back face;
   a photodetector system comprising:
      one or more photodetectors optically coupled to the scintillator compartment and configured to detect scintillation photons generated in the scintillating medium; and
      one or more reflecting surfaces configured to reflect scintillation photons generated in the scintillating medium to the one or more photodetectors;
   an optical imaging system comprising:
      one or more excitation light sources optically coupled to the scintillator compartment and configured to direct excitation light onto the scintillating medium; and
   one or more fluorescence detectors optically coupled to the scintillator compartment and configured to detect fluorescence generated by the fluors in the scintillating medium, the method comprising:
   positioning a sample within an imaging volume defined by the plurality of imaging modules, wherein positron-electron annihilation events in the sample generate coincident gamma-ray pairs;
   detecting coincident gamma-ray pairs arriving at a pair of imaging modules using the time-of-flight photodetector system by detecting scintillation photons generated when a first gamma-ray of a coincident gamma-ray pair interacts with the scintillating media in a first imaging module and a second gamma-ray of the coincident gamma-ray pair interacts with the scintillating medium in a second imaging module within a coincidence time window;
   initiating a sequence of steps for the first and second imaging modules of each pair of imaging modules that detects a coincident gamma-ray pair, the sequence of steps comprising:
      triggering a recording of scintillation light by the time-of-flight photodetector system;
      interrogating the scintillating medium by directing excitation light from the one or more excitation light sources onto the scintillating medium, wherein the excitation light excites fluors that have been activated by ionization energy deposited in the scintillating medium by Compton electrons;
      recording fluorescence emitted by the excited fluors to generate images of energy clusters corresponding to Compton scatters of the first gamma ray in the scintillating medium of the first imaging module and images of energy clusters corresponding to Compton scatters of the second gamma-ray in the scintillating medium of the second imaging module;
      identifying a location of a first collision for the first gamma-ray in the scintillating medium of the first imaging module and a location of a first collision for the second gamma-ray in the scintillating medium of the second imaging module; and
      forming a line-of-response between the location of the first collision for the first gamma-ray and the location of the first collision for the second gamma-ray; and
   generating an image of a spatial distribution of the positron-electron annihilation events within the sample based on the lines-of-response.

6. The method of claim 5, wherein the sample is a non-human.

7. The method of claim 5, wherein the sample is a human.

8. The method of claim 5, wherein the photodetector system is a time-of-flight photodetector system, and the method further comprises calculating a most likely longitudinal position, and an associated longitudinal resolution of the longitudinal position, for the positron-electron annihilation event along the line-of-response, based on arrival times of the first and second gamma-rays measured by the time-of-flight photodetector system and measurement uncertainties for the locations of the first collisions.

9. The method of claim 8, wherein the line-of-response is characterized by an initial transverse resolution, and the method further comprises improving the initial transverse resolution of the line-of-response and the longitudinal resolution along the line-of-response based on a totality of spatial information from the images generated by the optical imaging system and temporal information generated by the time-of-flight photodetector system for the Compton scatters of the first and second gamma-rays.

10. The method of claim 5, further comprising detecting Cherenkov radiation generated when a first gamma-ray of a coincident gamma-ray pair interacts with the scintillating medium in a first imaging module and a second gamma-ray of the coincident gamma-ray pair interacts with the scintillating medium in a second imaging module.

11. The method of claim 5, wherein the images generated by the optical imaging system provide images of tracks of individual Compton electrons in the scintillating medium, and the images of the tracks reveal one or more of the following track attributes for said Compton electrons: a) an initial Compton-electron direction in the scintillating medium; b) a range of the Compton electron; c) locations of multiple Compton scatters along the track; d) a location of a terminal Compton scatter of the track; and e) total ionization energy deposited by the Compton scatters in the scintillating medium.

12. The method of claim 5, wherein the images generated by the optical imaging system reveal a direction of a gamma-ray after it undergoes a Compton scatter by identifying an origin of a path of said gamma-ray at said Compton scatter and a termination of the path of said gamma-ray at a location of a subsequent Compton scatter.

13. The method of claim 5, wherein the step of identifying the location of the first collision for the first gamma-ray in the scintillating medium of the first imaging module and the location of the first collision for the second gamma-ray in the scintillating medium of the second imaging module comprises determining a time-ordering of the Compton scatters of the first and second gamma-rays based on Compton kinematics.

14. The method of claim 13, wherein application of the Compton kinematics comprises:
   calculating a relative probability for each of multiple permutations of a time-ordered chain of successive Compton scatters along paths of the first and second gamma-rays based on relative Compton scatter locations and angles and Compton scattering kinematic constraints;
   identifying a most probable first Compton scatter;
   identifying a starting point for a track of a Compton electron produced by said first Compton scatter as the location of the first collision;
   determining a direction of the first Compton electron; and
   determining an energy of the first Compton electron.

15. The method of claim 5, further comprising identifying coincident gamma-ray pairs that have undergone in-sample scattering.

16. The method of claim 15, wherein a coincident gamma-ray pair that has undergone in-sample scattering is identified by assigning an event weight to the coincident gamma-ray pair based on one or more of:
   (a) a non-zero component of the line-of-response normal to a plane defined by directions of the gamma-ray and a Compton electron at the locations of the first collisions for the first and second gamma-rays;
   (b) a deviation from 511 keV of a best-fit energy for the first or second gamma-ray, as determined from a most probable time-ordered chain of successive Compton scatters along paths of the first and second gamma-rays and the line-of-response;
   (c) an angle between scattering planes of the first and second gamma-rays of the coincident gamma-ray pair; and (d) respective path lengths through the sample of the first and second gamma-rays of the coincident gamma-ray pair.

17. The positron emission tomography system of claim 1, wherein the photodetector system of at least one of the imaging modules is a time-of-flight photodetector system.

18. The positron emission tomography system of claim 17, wherein the time-of-flight photodetector system is capable of resolving single photons with a time resolution of less than 50 psec.

19. The positron emission tomography system of claim 17, wherein the time-of-flight photodetector system has a readout system with a sampling rate of at least 5 Gs/s.

20. The positron emission tomography system of claim 1, wherein the one or more excitation light sources comprise one or more lasers.

21. The positron emission tomography system of claim 1, wherein the one or more fluorescence detectors comprise one or more digital cameras.

* * * * *